US009932598B2

(12) United States Patent
Palsson et al.

(10) Patent No.: US 9,932,598 B2
(45) Date of Patent: Apr. 3, 2018

(54) METABOLIC ENGINEERING OF MICROBIAL ORGANISMS

(71) Applicant: The Regents of the University of California, Oakland, CA (US)

(72) Inventors: Bernhard O. Palsson, La Jolla, CA (US); Adam M. Feist, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 351 days.

(21) Appl. No.: 13/957,340

(22) Filed: Aug. 1, 2013

(65) Prior Publication Data

US 2014/0038296 A1 Feb. 6, 2014

Related U.S. Application Data

(60) Provisional application No. 61/742,218, filed on Aug. 2, 2012.

(51) Int. Cl.
*C12N 15/70* (2006.01)
*C12P 7/56* (2006.01)
*C12N 9/02* (2006.01)
*C12N 9/10* (2006.01)

(52) U.S. Cl.
CPC ............ *C12N 15/70* (2013.01); *C12N 9/0008* (2013.01); *C12N 9/1029* (2013.01); *C12P 7/56* (2013.01); *C12Y 102/04001* (2013.01); *C12Y 203/01054* (2013.01)

(58) Field of Classification Search
CPC .... C12N 15/70; C12N 9/0008; C12N 9/1029; C12Y 102/04001; C12Y 203/01054; C12P 7/56
See application file for complete search history.

(56) References Cited

PUBLICATIONS

Feist, Adam Michael. (2008). Model-driven metabolic engineering of *Escherichia coli*: a systems biology approach. UC San Diego: b6635952. Retrieved from: https://escholarship.org/uc/item/55w152gs.*
Oren, A."Prokaryote diversity and taxonomy: current status and future challenges." Philos Trans R Soc Lond B Biol Sci. Apr. 29, 2004;359(1444):623-38.*
Andersen, R. "Diversity of eukaryotic algae." Biodiversity & Conservation1, 267-292 (1992).*
Guiry, Michael. "How many species of algae are there?." Journal of Phycology, 48, 1057-1063.*
Wade, William. "Uncluturable bacteria—the uncharacterized organisms that cause oral infections" J R Soc Med. Feb. 2002; 95(2): 81-83.*

Zhu et al. "Homolactate fermentation by metabolically engineered *Escherichia coli* strains." Appl Environ Microbiol. Jan. 2007;73(2):456-64.*
Wang et al. "Programming cells by multiplex genome engineering and accelerated evolution." Nature. Aug. 13, 2009;460(7257):894-8.*
Feist A. "Model-Driven Metabolic Engineering of *Escherichia coli* : A Systems Biology Approach." University of California—San Diego. Presented Nov. 2008.*
Jeffrey David Orth. "Systems biology analysis of *Escherichia coli* for discovery and metabolic engineering." Publication Date Jan. 20, 2012. Retrieved from: http://escholarship.org/uc/item/3h74m1h6.*
Feist AM, "Model-Driven Metabolic Engineering of *Escherichia coli*: A systems biology approach". Powerpoint presentation from Thesis Defense, University of California, San Diego Department of Bioengineering, dated Nov. 25, 2008, in 47 pages.
Feist AM, Zielinski DC, Orth JD, Schellenberger J, Herrgard MJ, Palsson BO. Model-driven evaluation of the production potential for growth-coupled products of *Escherichia coli*. Metab Eng. 2010,12(3): pp. 173-186.
Acharya S, Foster PL, Brooks P, Fishel R. The coordinated functions of the *E. coli* MutS and MutL proteins in mismatch repair. Mol Cell 2003,12(1): pp. 233-246.
Alper H, Jin YS, Moxley JF, Stephanopoulos G. Identifying gene targets for the metabolic engineering of lycopene biosynthesis in *Escherichia coli*. Metab Eng 2005, 7(3): pp. 155-164.
Alper H, Miyaoku K, Stephanopoulos G. Construction of lycopene-overproducing *E. coli* strains by combining systematic and combinatorial gene knockout targets. Nat Biotechnol 2005, 23(5): pp. 612-616.
Bailey JE. Toward a science of metabolic engineering. Science 1991, 252(5013): pp. 1668-1675.
Becker SA, Feist AM, Mo ML, Hannum G, Palsson BO, Herrgard MJ. Quantitative prediction of cellular metabolism with constraint-based models: The COBRA Toolbox. Nat. Protocols 2007, 2(3): pp. 727-738.
Burgard AP, Pharkya P, Maranas CD. Optknock: a bilevel programming framework for identifying gene knockout strategies for microbial strain optimization. Biotechnol Bioeng 2003, 84(6): pp. 647-657.
Chang DE, Jung HC, Rhee JS, Pan JG. Homofermentative production of D- or L-lactate in metabolically engineered *Escherichia coli* RR1. Appl Environ Microbiol 1999, 65(4): pp. 1384-1389.
Datsenko KA, Wanner BL. One-step inactivation of chromosomal genes in *Escherichia coli* K-12 using products. Proc Natl Acad Sci U S A. 2000, 97(12): pp. 6640-6645.
Dien BS, Nichols NN, Bothast RJ. Recombinant *Escherichia coli* engineered for production of L-lactic acid from hexose and pentose sugars. J Ind Microbiol Biotechnol 2001, 27(4): pp. 259-264.
Feist AM, Henry CS, Reed JL, Krummenacker M, Joyce AR, Karp PD, Broadbelt LJ, Hatzimanikatis V, Palsson BO. A genome-scale metabolic reconstruction for *Escherichia coli* K-12 MG1655 that accounts for 1260 ORFs and thermodynamic information. Mol Syst Biol 2007, 3(121). pp. 1-18.
Feist AM, Herrgard MJ, Thiele I, Reed JL, Palsson BO.. Reconstruction of biochemical networks in microbial organisms. Nat Rev Microbiol Feb. 2009, 7: pp. 129-143.
Feist AM, Palsson BO. The growing scope of applications of genome-scale metabolic reconstructions using *Escherichia coli*. Nat Biotech 2008, 26(6): pp. 659-667.

(Continued)

*Primary Examiner* — Titilayo Moloye
(74) *Attorney, Agent, or Firm* — Knobbe, Martens, Olson & Bear, LLP

(57) ABSTRACT

Microbial strains with desirable carbohydrate productions characteristics and methods of making and using the same are provided herein.

18 Claims, 5 Drawing Sheets

(56) References Cited

PUBLICATIONS

Fong SS, Burgard AP, Herring CD, Knight EM, Blattner FR, Maranas CD, Palsson BO. In silico design and adaptive evolution of *Escherichia coli* for production of lactic acid. Biotechnol Bioeng 2005, 91(5): pp. 643-648.

Fong SS, Marciniak JY, Palsson BØ. Description and Interpretation of Adaptive Evolution of *Escherichia coli* K-12 MG1655 Using a Genome-scale in silico Metabolic Model. Journal of Bacteriology 2003, 185(21): pp. 6400-6408.

Fong SS, Palsson BO. Metabolic gene-deletion strains of *Escherichia coli* evolve to computationally predicted growth phenotypes. Nat Genet 2004, 36(10): pp. 1056-1058.

Giraud A, Matic I, Tenaillon O, Clara A, Radman M, Fons M, Taddei F. Costs and benefits of high mutation rates: adaptive evolution of bacteria in the mouse gut. Science 2001, 291(5513): pp. 2606-2608.

Herring CD, Raghunathan A, Honisch C, Patel T, Applebee MK, Joyce AR, Albert TJ, Blattner FR, van den Boom D, Cantor CR and others. Comparative genome sequencing of *Escherichia coli* allows observation of bacterial evolution on a laboratory timescale. Nat Genet 2006, 38(12): pp. 1406-1412.

Hofvendahl K, Hahn-Hagerdal B. Factors affecting the fermentative lactic acid production from renewable resources1. Enzyme and Microbial Technology 2000, 26(2-4): pp. 87-107.

Ibarra RU, Edwards JS, Palsson BO. *Escherichia coli* K-12 undergoes adaptive evolution to achieve in silico predicted optimal growth. Nature2002,420(6912): pp. 186-189.

Lee KH, Park JH, Kim TY, Kim HU, Lee SY. Systems metabolic engineering of *Escherichia coli* for L-threonine production. Mol Syst Biol 2007, 3: p. 149.

Lee SJ, Lee DY, Kim TY, Kim BH, Lee J, Lee SY. Metabolic engineering of *Escherichia coli* for enhanced production of succinic acid, based on genome comparison and in silico gene knockout simulation. Appl Environ Microbiol 2005, 71(12): pp. 7880-7887.

Lee SY, Kim JM, Song H, Lee JW, Kim TY, Jang YS. From genome sequence to integrated bioprocess for succinic acid production by Mannheimia succiniciproducens. Appl Microbiol Biotechnol 2008, 79(1): pp. 11-22.

Lee SY, Papoutsakis ET., eds. Metabolic Engineering: Marcel Dekker, Inc. New York. 1999.

Neidhardt FC, editor. *Escherichia coli* and *Salmonella*: cellular and molecular biology. 2nd ed. Washington, D.C.: ASM Press. 1996.

Oh YK, Palsson BO, Park SM, Schilling CH, Mahadevan R.. Genome-scale reconstruction of metabolic network in bacillus subtilis based on highthroughput phenotyping and gene essentiality data. J Biol Chem. 2007, 82(9): pp. 28791-28799.

Park JH, Lee KH, Kim TY, Lee SY, Metabolic engineering of *Escherichia coli* for the production of L-valine based on transcriptome analysis and in silico gene knockout simulation. Proc Natl Acad Sci U S A 2007,104(19): pp. 7797-7802.

Park JH, Lee SY, Kim TY, Kim HU. Application of systems biology for bioprocess development. Trends Biotechnol 2008. 26(8): pp. 404-412.

Patil KR, Rocha I, Forster J, Neilsen J. Evolutionary programming as a platform for in silico metabolic engineering. BMC Bioinformatics 2005, 6: p. 308.

Price ND, Reed JL, Palsson BO. Genome-scale models of microbial cells: evaluating the consequences of constraints. Nat Rev Microbiol 2004, 2(11), pp. 886-897.

Reed JL, Patel TR, Chen KH, Joyce AR, Applebee MK, Herring CD, Bui OT, Knight EM, Fong SS, Palsson BO. Systems approach to refining genome annotation. Proc Natl Acad Sci U S A 2006, 103(46): pp. 17480-17484.

Schlensog V, Bock A. The *Escherichia coli* fdv gene probably encodes mutS and is located at minute 58.8 adjacent to the hyc-hyp gene cluster. J Bacteriol 1991, 173(23): pp. 7414-7415.

Shaver AC, Dombrowski PG, Sweeney JY, Treis T, Zappala RM, Sniegowski PD. Fitness evolution and the rise of mutator alleles in experimental *Escherichia coli* populations. Genetics 2002,162(2): pp. 557-566.

Stephanopoulos G, Nielsen J, Aristidou A. 1998. Metabolic Engineering. San Diego: Academic Press.

Varma A, Palsson BO. Stoichiometric flux balance models quantitatively predict growth and metabolic by-product secretion in wild-type *Escherichia coli* W3110. Applied and Environmental Microbiology 1994. 60(10): pp. 3724-3731.

Wang Q, Chen X, Yang Y, Zhao X. Genome-scale in silico aided metabolic analysis and flux comparisons of *Escherichia coli* to improve succinate production. Appl Microbiol Biotechnol 2006. V73(4): pp. 887-894.

Zhou S, Causey TB, Hasona A, Shanmugam KT, Ingram LO. Production of Optically Pure D-Lactic Acid in Mineral Salts Medium by Metabolically Engineered *Escherichia coli* W3110. Appl. Environ. Microbiol. 2003. 69(1): pp. 399-407.

Zhu Y, Eiteman MA, DeWitt K, Altman E. Homolactate fermentation by metabolically engineered *Escherichia coli* strains. Appl Environ Microbiol 2007. 73(2): pp. 456-464.

NCBI Gene search results for "pFLA" [Gene Name] entries with a creation date on or before Aug. 1, 2013, printed from the world wide web at https://www.ncbi.nlm.gov/gene on Mar. 11, 2016, in 10 pages.

NCBI Gene search results for "pFLB" [Gene Name] entries with a creation date on or before Aug. 1, 2013, printed from the world wide web at https://www.ncbi.nlm.gov/gene on Mar. 11, 2016, in 3 pages.

NCBI Gene search results for "pFLC" [Gene Name] entries with a creation date on or before Aug. 1, 2013, printed from the world wide web at https://www.ncbi.nlm.gov/gene on Mar. 11, 2016, in 2 pages.

NCBI Gene search results for "pFLD" [Gene Name] entries with a creation date on or before Aug. 1, 2013, printed from the world wide web at https://www.ncbi.nlm.gov/gene on Mar. 11, 2016, in 2 pages.

NCBI Protein search results for "pyruvate dehydrogenase" [Protein Name] with a publication date on or before Aug. 1, 2013, search results downloaded from the world wide web at https://www.ncbi.nlm.gov/protein on Mar. 16, 2016, also included is a screen shot of the search results page, summarizing the taxonomic groups included in the search, in 2467 pages.

NCBI Protein search results for "pyruvate formate lyase" [Protein Name] with a publication date on or before Aug. 1, 2013, search results downloaded from the world wide web at https://www.ncbi.nlm.gov/protein on Mar. 16, 2016, also included is a screen shot of the search results page, summarizing the taxonomic groups included in the search, in 1223 pages.

UniProtKB-POA9N4 (PFLA_ECOLI), Integrated Into UniProtKB/Swiss-Prot Jul. 19, 2006, and printed from the world wide web at www.uniprot.org/uniprot/P0A9N4 on May 2, 2017, in 7 pages. It is noted that this item refers to a web page, and may have been available in some form prior to the date on which it was printed.

UniProtKB-P09373 (PFLB_ECOLI), integrated into UniProtKB/Swiss-Prot Jul. 1, 1989, and printed from the world wide web at www.uniprot.org/uniprot/P09373 on May 2, 2017, in 9 pages. It is noted that this item refers to a web page, and may have been available in some form prior to the date on which it was printed.

UniProtKB-P32675 (PFLC_ECOLI), integrated into UniProtKB/Swiss-Prot Oct. 1, 1993, and printed from the world wide web at www.uniprot.org/uniprot/P32675 on May 2, 2017, in 7 pages. It is noted that this item refers to a web page, and may have been available in some form prior to the date on which it was printed.

UniProtKB-P32674 (PFLD_ECOLI), integrated into UniProtKB/Swiss-Prot Oct. 1, 1993, and printed from the world wide web at www.uniprot.org/uniprot/P32674 on May 2, 2017, in 7 pages. It is noted that this item refers to a web page, and may have been available in some form prior to the date on which it was printed.

UniProtKB-POAC23 (FOCA_ECOLI), integrated into UniProtKB/Swiss-Prot Nov. 8, 2005, and printed from the world wide web at www.uniprot.org/uniprot/P0AC23 on May 2, 2017, in 7 pages. It is noted that this item refers to a web page, and may have been available in some form prior to the date on which it was printed.

\* cited by examiner

METABOLIC ENGINEERING OF MICROBIAL ORGANISMS

RELATED APPLICATIONS

The present application claims the benefit of U.S. Provisional Application No. 61/742,218, filed on Aug. 2, 2012, which is hereby incorporated by reference in its entirety. The present application is related to U.S. Provisional Application No. 61/401,017, filed Aug. 4, 2010, and U.S. Provisional Application No. 61/273,426, filed Aug. 3, 2009, each of which is hereby incorporated by reference in its entirety.

SEQUENCE LISTING AND TABLES IN ELECTRONIC FORMAT

The present application is being filed along with a Sequence Listing in electronic format. The Sequence Listing is provided as a file entitled UCSD033001ASEQUENCE.txt, last saved Aug. 1, 2013, created on Jul. 31, 2013, which is 53,033,897 bytes in size. The information in the electronic format of the Sequence Listing is incorporated herein by reference in its entirety.

BACKGROUND

Through the process of metabolic engineering, microbial organisms can be engineered for the production of various desirable compounds. Such engineered microbial strains and their products can be useful. For example, some microbial strains can produce chemicals from renewable feedstocks rather than from nonrenewable petroleum. Metabolic engineering has been practiced for many years, and the traditional approaches have included strategies such as random mutagenesis with selection for an over-producer or over-expression of genes either directly responsible for secondary metabolite production or genes indirectly involved in increasing metabolite production. Provided herein are engineered microbial strains with useful carbohydrate production characteristics. In some embodiments, the engineered microbial strains are designed using a genome-scale metabolic model so as to systematically select a strain with a desired phenotype.

FIELD

The field relates generally to genetically engineered microbial organisms. In some embodiments, microbial organisms genetically engineered for high-yield production of carbohydrates are provided.

SUMMARY

In one embodiment, a genetically engineered microbial organism comprising a genetic modification which substantially reduces pyruvate format lyase (PFL) activity and a genetic modification which substantially reduces pyruvate dehydrogenase (PDH) activity is provided. In some aspects of this embodiment, the production of carbohydrates comprises producing D-lactate from a glucose precursor. In some aspects of this embodiment, the genetic modification which substantially reduces PFL activity reduces PFL activity by at least about 70%. In some aspects of this embodiment, the genetic modification which substantially reduces PDH activity reduces PDH activity by at least about 70%. In some aspects of this embodiment, the genetic modification which substantially reduces PFL activity reduces PFL activity by at least about 90%, and wherein the genetic modification which substantially reduces PDH activity reduces PDH activity by at least about 90%. In some aspects of this embodiment, the genetic modification which substantially reduces PFL activity eliminates PFL activity, and wherein the genetic modification which substantially reduces PDH activity eliminates PDH activity. In some aspects of this embodiment, the microbial organism has undergone adaptive evolution. In some aspects of this embodiment, the genetically engineered microbial organism further comprises a genetic modification that increases that increases the mutation rate of the microbial organism at least about 2-fold per generation. In some aspects of this embodiment, the genetic modification that increases the mutation rate comprises a loss-of-function mutation in the mutS gene. In some aspects of this embodiment, the genetic modification which substantially reduces PFL activity is selected from the group consisting of: a hypomorphic mutation in each of pflABfocA and pflDC, a phenotypic null mutation in each of pflABfocA and pflDC, a deletion of each of pflABfocA and pflDC, a hypomorphic mutation in pflABfocA and a deletion of pflDC, a deletion of pflABfocA and a hypomorphic mutation in pflDC, a hypomorphic mutation in pflABfocA and a phenotypic null mutation in pflDC, a null mutation in pflABfocA and a hypomorphic mutation in pflDC, a deletion of in pflABfocA and a null mutation in pflDC, and a phenotypic null mutation in pflABfocA and a deletion of pflDC. In some aspects of this embodiment, the genetic modification which substantially reduces PDH activity is selected from the group consisting of a hypomorphic mutation in aceEF, a null mutation in aceEF, and a deletion of aceEF. In some aspects of this embodiment, the genetic modification which substantially reduces PFL activity comprises a deletion of each of pflABfocA and pflDC, and wherein the genetic modification eliminating PDH activity comprises a deletion of aceEF. In some aspects of this embodiment, the organism comprises a genotype of: pflABfocA pflDC aceEF xylFGH rbsACB alsBAC mutS. In some aspects of this embodiment, the organism is of one of the BOP384eG1 strain or BOP384eG2 strain. In some aspects of this embodiment, the genetically engineered microbial further comprises deletion of each of a native xylGFH, rbsACB, and alsBAC operon. In some aspects of this embodiment, the genetically engineered microbial organism further comprises at least one mutation selected from the group consisting of: 1022011 C→T, 111897 G→A, 1135244 A→G, 1137595 A→G, 1163111 A→G, 1247873 G→A, 1260197 C→T, 1274794 T→C, 1386732 A→G, 1435247 Δ1 bp, 1440978 G→A, 1580390 A→, 1604028 T→C, 1610530+C, 1679479 T→C, 1682336 A→G, 1729483 G→A, 1760136 G→A, 1866695 G→A, 1929016 G→A, 1950262 G→A, 1976527 Δ776 bp, 2071288 G→A, 2085304+G, 2098010 T→C, 2257220 A→G, 2358479+C, 2405257 G→C, 2534334 Δ1::IS186 (−)+6 bp::Δ1, 2620968 Δ1 bp, 2662540 T→C, 2732557+C, 2740321 T→C, 2763809+C, 2767188 G→A, 2782127 A→G, 2809146+A, 2824039 T→C, 2826646 G→A, 2844070 G→A, 2926442+T, 2927497 G→A, 2932138 TA, 2965591 T→C, 2975919 T→C, 3114125 C→T, 3176882 G→A, 3218853 T→C, 3246033 G→A, 3268091 C→T, 3268123 CA, 3268165 C→T, 3279141 C→T, 3302829 Δ1 bp, 3315496 A→G, 3335733 C→T, 34111+T, 3429378 T→C, 345189 A→G, 3506796 T→C, 3526004 T→C, 3548297 T→C, 379237 Δ1 bp, 379237 Δ2 bp, 386281 C→T, 3955730 G→A, 3957957 C→T, 3978813 C→A, 3982057 C→T, 3983344 C→T, 3990407 Δ8 bp, 407943 A→G, 4105271 A→G, 4153541 A→G, 42111 C→A, 4234068 T→G, 4294403+CG, 4306572 3434 bp→82 bp, 4444833 A→G, 4503718 G→A, 454725 C→T, 4604230+G, 4604346 Δ1 bp, 507894 T→C, 533362 A→G, 547694 A→G, 547831+G, 558493 G→T, 560913+G, 619171 A→G, 653396 T→C, 696062 G→A, 700027 C→T, 700286+C, 700599+C, 700679+G, 751964 C→T, 760544 C→T, 844446 C→T, 852434+A, 922473+G, 961467 C→T, and 963462 A→G, with reference to SEQ ID NO: 1. In some aspects of this embodiment, the microbial organism comprises the mutations annotated in any one of SEQ ID NOs: 2-9. In some aspects of this embodiment, the genetically engineered microbial organism has a steady-state glucose uptake rate of at least about 30 mmol per gDW per hour under standard conditions in 1 g per liter yeast extract medium, for example at least about 30 mm per gDW per hour, 35, 40, 45, 50, 55, 60, 65, 70, 75, 80, 85, 90, 95, or 100 mm per gDW per hour. In some aspects of this embodiment, the microbial organism is a recombinant E. coli.

Another embodiment includes a method of producing a genetically engineered microbial organism that has a steady-state glucose uptake rate of at least about 30 mmol per gDW per hour in a medium comprising 1 g per liter yeast extract, and the method includes performing at least one cycle of adaptive evolution on a culture of a microbial organism as described herein. In some aspects of this embodiment, the adaptive evolution comprises at least one of steady-state evolution or serial passage exponential evolution. In some aspects of this embodiment, the adaptive evolution comprises at least 14 days of adaptive evolution. In some aspects of this embodiment, the adaptive evolution comprises at least 16 days of adaptive evolution. In some aspects of this embodiment, the steady-state glucose uptake is at least about 40 mmol per gDW per hour under standard conditions in 1 g per liter yeast extract medium.

Another embodiment includes a genetically engineered microbial organism comprising a genetic modification which reduces pyruvate format lyase (PFL) activity and a genetic modification which reduces pyruvate deghydrogenase (PDH) activity, in which the genetically engineered microbial organism has a steady-state glucose uptake rate of at least about 30 mmol per gDW per hour under standard conditions in 1 g per liter yeast extract medium.

DETAILED DESCRIPTION

Figure 1:
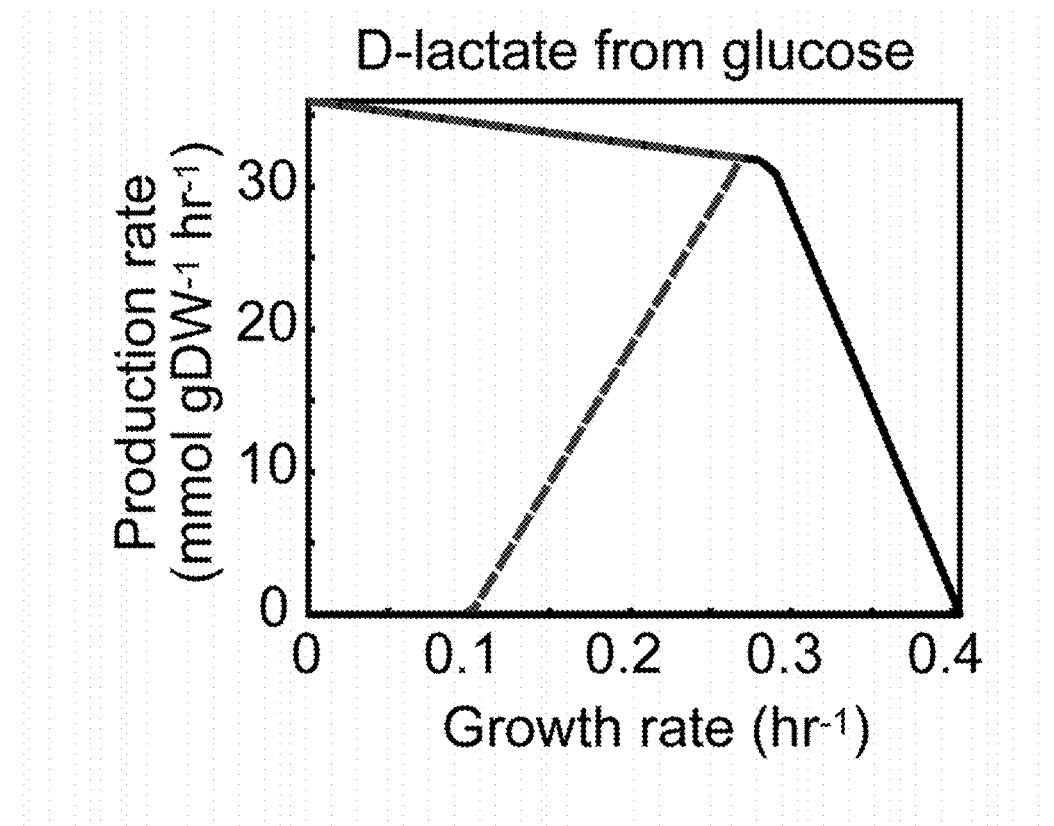
FIG. 1 is a graph illustrating the predicted production envelopes for strains constructed according to some embodiments herein. This production envelope was determined to be a superior design out of a pool of designs that was computationally generated. The glucose uptake rate is 18 mmol gDW$^{-1}$ hr$^{-1}$ (a typical wild-type anaerobic uptake rate) and minimal medium conditions were used

According to some embodiments herein, microbial organisms are provided. The microbial organism can be configured to produce a carbohydrate from a precursor. In some embodiments, the microbial organism includes mutations eliminating format lyase (PFL) activity and pyruvate dehydrogenase (PDH) activity. In some embodiments, the microbial organism is E. coli. In some embodiments, the microbial organism further undergoes adaptive evolution, and organisms with desired carbohydrate production characteristics are selected. To expedite adaptive evolution, the microbial organism can comprise at least one genetic modification that increases the mutation rate. In some embodiments, the mutation is a mutS mutation. In some embodiments, the microbial organism has at least a pflABfocA pflDC aceEF genotype. Optionally, the microbial organism can include additional mutations. In some embodiments the microbial organisms has a pflABfocA pflDC aceEF xylFGH rbsACB alsBAC mutS genotype.

Metabolic engineering is a growing field for which new methods are being developed to generate microbial products rapidly and efficiently. According to some embodiments, two approaches that can aid this process are analysis of growth-coupled production using constraint-based modeling, and adaptive evolution for strain optimization. In some embodiments, the constraint-based modeling may comprise the modeling described in U.S. Provisional Application No. 61/742,218, filed on Aug. 2, 2012, U.S. Provisional Application No. 61/401,017, filed Aug. 4, 2010, now expired, or U.S. Provisional Application No. 61/273,426, filed Aug. 3, 2009, the disclosure of each of which are hereby incorporated by reference in their entireties. In some embodiments the two approaches are combined, for example by selecting a strain identified from a model-driven analysis of the production of native microbial metabolites (for example, *Escherichia coli* metabolites, see Feist et al. 2010), evolving it using adaptive evolution, and characterizing its production capabilities. As such, in some embodiments, an engineered microbial strain is provided. In some embodiments adaptive evolutions results in a substantial increase in growth rate and/or substrate consumption rate for this strain. In some embodiments, the production phenotype of this strain is similar to the computationally predicted phenotype. In some embodiments, the production phenotype of this strain is similar to the computationally predicted phenotype, for example exhibiting substantial increases in growth rate and/or substrate consumption rate, and/or product production rate.

Carbohydrates

Lactic acid (and its corresponding lactate ions, for example D-Lactate) is an industrially relevant chemical with many practical uses. In some embodiments, lactic acid or a derivative thereof is useful in the food and beverage industry as an acidulant or as a preservative, or in polylactic acid (PLA), a biodegradable plastic.

A variety of carbohydrates can be produced by microbial organisms from a variety of precursors (also referred to herein as "substrates") under a variety of conditions. In some embodiments, at least one of D-Lactate, Glycerol, L-Alanine, L-Serine, Pyruvate, Fumarate, L-Malate, Succinate, 2-Oxoglutarate, or L-Glutamate is produced by a microbial organism. In some embodiments, the carbohydrate is produced under aerobic conditions. In some embodiments, the carbohydrate is produced under anaerobic conductions. In some embodiments, the carbohydrate is produced from a precursor, for example glucose or xylose. In some embodiments, D-lactate is produced from a glucose precursor.

Genetic Modifications

A variety of genetic modifications, for example mutations, can be provided according to some embodiments herein. A genetic locus in a microbial organism can produce one or more gene products. In some embodiments, the gene product is a nucleic acid, for example a ribosomal RNA. In some embodiments, the gene product is a polypeptide.

A genetic modification affecting one or more genetic loci can cause a loss-of-function in the gene product, a gain-of-function in the gene product, and/or can cause the gene product to adopt a new function. In some embodiments, a loss-of-function mutation is provided that reduces, but does not eliminate activity of the gene product (this class of mutation can also be referred to herein a "hypomorphic" mutation or "partial loss-of-function" mutation). In some embodiments, a loss-of-function mutation substantially reduces gene product activity. As used herein, "substantially reduces" gene product activity and variations of this root term refer to at least a 50% reduction in gene product activity compared to wild-type, for example, a 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, 99.99%, or 99.999% reduction. In some embodiments, a loss-of-function mutation eliminates gene product activity (this class of mutation can also be referred to herein as a "null" mutation). In some embodiments, a null mutation eliminates at least the gene-product-encoding sequence of a genetic locus. In some embodiments a null mutation eliminates the entire genetic locus. While a deletion of a genetic locus is a type of null mutation, null mutations can also encompass other sorts of genetic modifications. In some embodiments, a null mutation does not eliminate gene-product-encoding sequence, but prevents expression of the gene product (for example, by eliminating a promoter, a translation start sequence, or introducing an early stop codon). In some embodiments, a null mutation does not eliminate gene-product-encoding sequence or expression of a gene product, but eliminates or substantially eliminates activity of the gene product (for example, by mutating one or more catalytic residues from a protein). This latter class of null mutation may also be referred to herein as a "phenotypic null," or variations of this root term. In some embodiments, a loss-of-function mutation is a dominant negative mutation.

In addition to mutation of a genetic locus, other genetic modifications can also reduce or eliminate gene activity. By way of non-limiting example, antisense oligonucleotides can reduce or eliminate activity of the target gene. In some embodiments, a genetic modification for reducing gene expression comprises at least one antisense oligonucleotide. In some embodiments, an antisense oligonucleotide comprises an RNA complementary to at least a portion of a transcript of a target gene. In some embodiments, a microbial cell is genetically modified to express an antisense RNA directed to at least one transcript of the target gene. Additional exemplary genetic modifications that can be used to reduce gene activity in accordance with some embodiments herein include ribozymes, transcriptional repressors, inducible promoters, proteases directed to polypeptide encoded by a target gene, and the like.

In some embodiments, a mutation or genetic modification eliminates the activity of two or more gene products. In some embodiments, a mutation deletes an operon. In some embodiments, a mutation eliminates activity of one gene, and as a result, also eliminates activity of a second gene (for example, if the products of gene A and gene B function as a dimer, the elimination of either of gene A activity or gene B activity can also eliminate activity of the other gene).

A variety of techniques for making mutations are known to the skilled artisan. In some embodiments, a desired mutation is introduced via homologous recombination. A variety of vectors can be used for homologous mutation, for example phage or viral vectors, plasmid vectors, artificial chromosomes, and the like. In some embodiments, the vector is a pKD46, pKD13, or pCP20 plasmid, or variant thereof. In some embodiments, homologous sequences on a vector flank a genetic locus that can be used to identify homologous recombinants, for example an antibiotic resistance marker (for example, but not limited to kanamycin, chloramphenicol, or ampicillin resistance) or metabolic enzyme that permits an auxotroph to survive in a particular minimal medium. In some embodiments, mutations are introduced into at least a genome are random, and mutant microbial organisms having the desired mutations are selected.

In some embodiments, a host genome or portion thereof is synthesized, and introduced into a microbial organism. In some embodiments an entire host genome having the desired genetic features is synthesized and inserted into a microbial cell (see, e.g. Gibson et al., Science 2: 329, pp. 52-56, hereby incorporated by reference in its entirety).

Metabolic Engineering

In some embodiments, a systems biology based approach to metabolic engineering comprises growth-coupled design, in which the production of a metabolite by a microbial strain increases as growth rate increases (Burgard et al. 2003). Some traditional strain designs have relied on genetic manipulations that alter the metabolism in a way that typically redirects metabolic flux from producing biomass to producing a specific desired product. Without being limited by any particular theory, such strains can be highly unstable, and if left unsupported, mutations that increase growth rate at the cost of production can occur, and the strain can lose productivity over time. Furthermore, it is unusual for the increased secretion of a metabolic by-product alone to simultaneously increase growth rate. However, according to some embodiments, genome-scale metabolic models and constraint-based analysis methods can predict genetic manipulations that couple production objectives to a selection pressure (i.e., growth rate). Laboratory adaptive evolution can then be used as a tool to optimize in vivo strain designs.

OptKnock (Burgard et al. 2003) and OptGene (Patil et al. 2005) are two in silico algorithms, either or both of which can be used for designing growth-coupled strains according to some embodiments herein. Several OptKnock designs for the production of lactic acid have been constructed and adaptively evolved in vivo, and it was found that the experimental results closely agreed with the computational predictions (Fong et al. 2005). An in silico screen of the growth-coupled design potential of E. coli was conducted utilizing the genome-scale metabolic reconstruction and model iAF1260 and the aforementioned design algorithms (Feist et al. 2010). As such, in some embodiments, an iAF1260 model of E. coli is provided. According to some embodiments herein, a growth-coupled design for producing a carbohydrate is identified. In some embodiments, the carbohydrate is D-lactate. This design may be based on computationally predicted properties such as high predicted product yield, ability to produce and secrete only one compound (homofermentation), and use of well characterized metabolic pathways to produce the targeted product. According to some embodiments herein, computationally driven growth-coupled strain design processes are followed by construction of a strain in vivo, optimization of this strain through the adaptive evolution process, and characterization of its production phenotype.

Processes developed in accordance with some embodiments herein can result in generation of a computationally-predicted production strain design. In some embodiments, a metabolic reconstruction of a microbial organism is provided. By way of non-limiting example, organisms for which metabolic reconstructions are available are listed in Feist et al. 2008a (hereby incorporated by reference in its entirety), for example Bacillus subtilis (described in Oh et al. 2007, hereby incorporated by reference in its entirety). In some embodiments, a strain design is based on a metabolic reconstruction of E. coli. In some emboidments, a strain design is based on a metabolic reconstruction of B. subtilis.

In some embodiments, a compound, precursor, and/or production strain design is selected from the designs identified from the screen of native compounds used in Feist et al. 2010. The methods described herein can be readily applied to generate further strains of E. coli or other microbial organisms. In some embodiments, a previously-described strain design is used as a starting point for a strain design according to embodiments herein. For example, the analyzeGCdesign algorithm can apply a penalty for knockouts and can be applied to reduce the total number of genetic loci mutated in a strain design. As such, in some embodiments, the analyzeGCdesign algorithm is applied to an existing strain design. In some embodiments, the analyzeGCdesign algorithm has a knockout penalty of 90%. In some embodiments, the analyzeGCdesign algorithm is used to "streamline" a particular strain design so as to minimize the number of mutations for arriving at a desired characteristic.

Adaptive Evolution

In some embodiments, the microbial strain undergoes adaptive evolution. As used herein, adaptive evolution refers to obtaining one or more organisms with one or more desired characteristics through selection for the desired characteristics. It is contemplated that unless explicitly stated otherwise herein, "selection for a desired characteristic" and variations of this root phrase encompasses both positive selection for a desired characteristic and selection against an undesired characteristic. In some embodiments, the selected characteristic comprises at least one of growth rate, consumption of substrate, production rate of carbohydrate, or production efficiency of carbohydrate. In some embodiments, direct selection for the desired characteristic is performed. In some embodiments, at least one desired characteristic is coupled to at least one other characteristic, and selection is performed for the other characteristic. In some embodiments, the other characteristic is also a desired characteristic. In some embodiments, the other characteristic is a neutral characteristic (for example a marker, or a reporter molecule).

It is contemplated herein the coupling of microbial growth and target molecule production can facilitate adaptive evolution. In some embodiments, production of target molecule (for example carbohydrate) by a strain is growth-coupled to biomass production. Without being limited by any particular theory, the strain can be required to produce target molecule in order to produce biomass, so that achievement of faster growth can require secretion of the target molecule. As such, selection for faster growth can also select for increased secretion of target molecule.

Serial passage selection (also referred to as "serial passage exponential" or "SPE" selection) can result in optimization of the strain for target production as well as growth rate. In some embodiments, adaptive evolution comprises serial passage selection. In some embodiments, growth is coupled to target product secretion, and selection is performed for growth. The selection can be performed by serial passage selection. Protocols for serial passage are described in Fong, et al. 2005. Biotechnol Bioeng 91(5):643-8; Ibarra et al., Nature 420:186-9; Fong et al. 2003. Journal of Bacteriology 185(21):6400-8; Herring et al., 2006. Nat Genet. 38(12):1406-1412; and Fong and Palsson, 2004. Nat Genet. 36(10):1056-58, each of which is hereby incorporated by reference in its entirety. Serial passage selection can comprise passaging cells so that the cells remain in exponential growth phase, and never (or almost never) reach stationary phase. By way of non-limiting example, cells can be transferred when they reach a certain optical density that is characteristic of the cells being in exponential growth phase. In some embodiments, serial passage selection can comprise sufficiently large transfer volumes so as to reduce the chance of fixation of hitchhiker mutations. In some embodiments, serial passage selection is performed in batch cultures. In some embodiments, serial passage selection is performed to select for microbial organisms with increased carbohydrate production. In some embodiments, serial passage selection is performed to select for microbial organisms with increased D-lactate production. In some embodiments, at least 2 rounds of serial passage selection are performed, for example 2, 3, 4, 5, 6, 7, 8, 9, 10, 11, 12, 13, 14, 15, 16, 17, 18, 19, 20, 30, 40, 50, 60, 70, 80, 90, 100, 150, 200, 250, 300, 350, 400, 450, 500, 600, 700, 800, 900, or 1000 rounds of serial passage selection, including ranges between any two of the listed values.

In some embodiments, adaptive evolution includes steady state evolution. Steady state evolution can comprise gradually increasing the strength of a selective pressure in order to select for at least one desired characteristic. In some embodiments steady state evolution is provided to alleviate auxotropy for one or more metabolites. In some embodiments, concentrations of metabolite are gradually decreased in continuous culture. In some embodiments, the continuous culture is performed for at least 1 day, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 days, including ranges between any two of the listed values.

Without being limited by any particular theory, in some circumstances, adaptive evolution can be accelerated by increasing the mutation rate. As such, in some embodiments a microbial stain is engineered to have an increased mutation rate. In some embodiments, the microbial strain comprises a mutation that yields an increased mutation rate. By way of non-limiting example, the microbial strain can comprise the mutS mutation, which has been associated with increased mutation rate. In some embodiments, the microbial strain comprises a mutation (or combination of mutations) that increase the mutation rate by at least 1.2×, for example about 1.2×, 1.5×, 2×, 3×, 4×, 5×, 6×, 7×, 8×, 9×, 10×, 20×, 30×, 40×, 50×, 60×, 70×, 80×, 90×, 100×, 1000×, or 10000× compared to a reference strain lacking the mutation (or mutations) that increase the mutation rate. In some embodiments, after a strain with one or more desired characteristics is obtained through adaptive evolution, one or more mutations that increase the mutation rate are removed. In some embodiments, the mutations are replaced with wild-type sequence or functionally wild-type sequence. In some embodiments, the mutations are reverted.

Microbial Organisms

Microbial organisms and strains thereof are provided according to some embodiments herein. As used herein, "microbial organism," "microorganism," and the like refers to single cell prokaryotic, eukaryotic, and archaea. Exemplary microbial organisms include, but are not limited to, *Escherichia coli, Bacillus* species, *Pseudomonas* species, *Salmonella* species, *Rhodococcus* species, *Lactobacillus* species, *Enterococcus* species, *Alcaligenes* species, *Klebsiella* species, *Paenibacillus* species, *Arthrobacter* species, *Corynebacterium* species, *Brevibacterium* species, *Saccharomyces* species, *Pichia* species, *Candida* species, *Hansenula* species, *Cyanobacteria* species, *Bacillus subtilis, Bacillus licheniformis, Alcaligenes eutrophus, Paenibacillus macerans, Rhodococcus erythropolis, Pseudomonas putida, Lactobacillus plantarum, Enterococcus faecium, Enterococcus gallinarium*, and *Enterococcus faecalis*. In some embodiments, the microbial organism is a *Bacillus* species, for example *B. subtilis*. In some embodiments, the microbial organism is *E. coli*.

In some embodiments, a genetically engineered microbial organism comprising a genetic modification which substantially reduces pyruvate format lyase (PFL) activity and a genetic modification which substantially reduces pyruvate dehydrogenase (PDH) activity is provided. Without being limited by any particular theory, in some embodiments, removal of only two metabolic reactions can provide higher carbohydrate uptake than removal of three or more metabolic reactions. In some embodiments, the strain comprises a pflABfocA pflDC aceEF genotype or a genotype conferring a phenotype corresponding to that resulting from a pflABfocA pflDC aceEF genotype. According to some embodiments herein, a pflABfocA pflDC aceEF strain comprises one or more additional genetic modifications. In some embodiments, the strain comprises one or more antibiotic resistance markers such as kanR (also notated herein as "kan+"). In some embodiments, the strain comprises mutations in additional genetic loci, for example the operons that permit growth on xylose (for example, by knockouts of one or more of the xylFGH, rbsABC, or alsBAC operons).

In some embodiments, a microbial strain as shown in Table II is provided. In some embodiments, the strain is one of BOP330, BOP336, BOP338, BOP370, BOP372, BOP374, BOP 374e, BOP384, BOP384e1, BOP384eG2. In some embodiments, the strain is BOP374e. In some embodiments, the strain is BOP384eG1. In some embodiments, the strain is BOP384eG2. Any of strains BOP374e, BOP384eG1, and BOP384eG2 or any of the other strains described herein can be deposited in an acceptable depository under the Budapest Treaty on the International Recognition of the Deposit of Microorganisms for the Purposes of Patent Procedure.

In some embodiments, a genetically engineered microbial organism comprising a genetic modification which substantially reduces pyruvate format lyase (PFL) activity and a genetic modification which substantially reduces pyruvate dehydrogenase (PDH) activity is provided, and further comprises at least one of the mutations listed in Table VIa. In some embodiments, the strain further comprises at least one mutation selected from the group consisting of (each numerical position listed is with reference to SEQ ID NO: 1): C→T, 111897 G→A, 1135244 A→G, 1137595 A→G, 1163111 A→G, 1247873 G→A, 1260197 C→T, 1274794 T→C, 1386732 A→G, 1435247 Δ1 bp, 1440978 G→A, 1580390 A→G, 1604028 T→C, 1610530+C, 1679479 T→C, 1682336 A→G, 1729483 G→A, 1760136 G→A, 1866695 G→A, 1929016 G→A, 1950262 G→A, 1976527 Δ776 bp, 2071288 G→A, 2085304+G, 2098010 T→C, 2257220 A→G, 2358479+C, 2405257 G→C, 2534334 Δ1::IS186 (−)+6 bp::Δ1, 2620968 Δ1 bp, 2662540 T→C, 2732557+C, 2740321 T→C, 2763809+C, 2767188 G→A, 2782127 A→G, 2809146+A, 2824039 T→C, 2826646 G→A, 2844070 G→A, 2926442+T, 2927497 G→A, 2932138 T→A, 2965591 T→C, 2975919 T→C, 3114125 C→T, 3176882 G→A, 3218853 T→C, 3246033 G→A, 3268091 C→T, 3268123 C→A, 3268165 C→T, 3279141 C→T, 3302829 Δ1 bp, 3315496 A→G, 3335733 C→T, 34111+T, 3429378 T→C, 345189 A→G, 3506796 T→C, 3526004 T→C, 3548297 T→C, 379237 Δ1 bp, 379237 Δ2 bp, 386281 C→T, 3955730 G→A, 3957957 C→T, 3978813 C→A, 3982057 C→T, 3983344 C→T, 3990407 Δ8 bp, 407943 A→G, 4105271 A→G, 4153541 A→G, 42111 C→A, 4234068 T→G, 4294403+C→G, 4306572 3434 bp-→82 bp, 4444833 A→G, 4503718 G→A, 454725 C→T, 4604230+G, 4604346 Δ1 bp, 507894 T→C, 533362 A→G, 547694 A→G, 547831+G, 558493 G→T, 560913+G, 619171 A→G, 653396 T→C, 696062 G→A, 700027 C→T, 700286+C, 700599+C, 700679+G, 751964 C→T, 760544 C→T, 844446 C→T, 852434+A, 922473+G, 961467 C→T, and 963462 A→G. It is noted that SEQ ID NO: 1 represents a genomic sequence of wild-type *E. coli* K-12 MG1655, but that it is contemplated that any or all of the indicated mutations (or a corresponding mutation in a respective host genome) can readily be applied to a different microbial strain or species as described herein. In some embodiments, the microbial strain comprises at least 2 of these mutations, for example 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 5, 54, 55, 56, 57, 58, 59, 60, 91, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, or 103 of these mutations, including ranges between any two of the listed values. In some embodiments, the microbial strain comprises all of the indicated mutations in one of BOP384' Day 0 (see SEQ ID NO: 2), BOP384G1D' Day 3 (see SEQ ID NO: 3), BOP384G1H' Day 5 (see SEQ ID NO: 4), BOP384G1N' Day 8 (see SEQ ID NO: 5), BOP384G1S' Day 10 (see SEQ ID NO: 6), BOP384G1X' Day 13 (see SEQ ID NO: 7), BOP384eG1' (isolate 1) Day 14 (see SEQ ID NO: 8), or BOP384eG1' (isolate 2) Day 14 (see SEQ ID NO: 9) as shown in Tables VIb and VIc. In some embodiments, the microbial strain comprises at least one fewer mutation than the set of mutations identified in BOP384' Day 0 (see SEQ ID NO: 2), BOP384G1D' Day 3 (see SEQ ID NO: 3), BOP384G1H' Day 5 (see SEQ ID NO: 4), BOP384G1N' Day 8 (see SEQ ID NO: 5), BOP384G1S' Day 10 (see SEQ ID NO: 6), BOP384G1X' Day 13 (see SEQ ID NO: 7), BOP384eG1' (isolate 1) Day 14 (see SEQ ID NO: 8), or BOP384eG1' (isolate 2) Day 14 (see SEQ ID NO: 9) as shown in Tables VIb and VIc, for example at least one, two, three, four, five, six, seven, eight, nine, or ten fewer mutations. In some embodiments, the microbial strain comprises the set of mutations identified in BOP384' Day 0 (see SEQ ID NO: 2), BOP384G1D' Day 3 (see SEQ ID NO: 3), BOP384G1H' Day 5 (see SEQ ID NO: 4), BOP384G1N' Day 8 (see SEQ ID NO: 5), BOP384G1S' Day 10 (see SEQ ID NO: 6), BOP384G1X' Day 13 (see SEQ ID NO: 7), BOP384eG1' (isolate 1) Day 14 (see SEQ ID NO: 8), or BOP384eG1' (isolate 2) Day 14 (see SEQ ID NO: 9) as shown in Tables VIb and VIc, plus at least one additional mutation identified in Table VIa, for example one, two, three, four, five, six, seven, eight, nine, or ten additional mutations identified in Table VIa.

In some embodiments, a microbial strains as shown in Table II undergoes adaptive evolution. In some embodiments, a pflABfocA pflDC aceEF strain or a strain having a phenotype corresponding to that of a pflABfocA pflDC aceEF strain undergoes adaptive evolution. In some embodiments, a BOP338 strain undergoes adaptive evolution. In some embodiments, a BOP374e strain undergoes adaptive evolution.

It can be useful for a microbial strain to have desirable uptake and/or production characteristics under growing conditions that are adaptable to an industrial scale. In some embodiments, microbial strains as described herein have desirable production characteristics (e.g. product yield and volumetric productivity) at growth densities in a range consistent with industrial production. Exemplary descriptions of microbial strain production at industrial scales can be found in Chang et al. 1999; Dien et al. 2001; Zhou et al. 2003; and Zhu et al. 2007)

According to some embodiments herein, microbial strains with carbohydrate uptake and/or production capabilities near, at, or above the theoretical maximum are provided. In some embodiments, the theoretical production maximum of a microbial strain is as provided in Feist et al., 2010. In some embodiments, lactate production strains as provided herein provide superior performance in terms of production rate, growth rate, and/or byproduct formation as compared to other lactate-producing strains. In some embodiments, lactate production strains as provided herein provide superior performance in terms of production rate, growth rate, and/or byproduct formation as compared to the theoretical maximum. Exemplary characteristics of lactate-producing strains can be found in Fong et al., 2005, Chang et al. 1999; Dien et al. 2001; Zhou et al. 2003; Zhu et al. 2007.

In some embodiments, a strain is provided having an uptake rate of at least about 30 mmol per grams dry weight per hour (mmol $gDW^{-1}$ $hr^{-1}$) under standard conditions in 1 g per liter yeast extract medium, for example about 30 mmol $gDW^{-1}$ $hr^{-1}$, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mmol $gDW^{-1}$ $hr^{-1}$, including ranges between any two of the listed values. In some embodiments, the strain may provide more than 100 mmol $gDW^{-1}$ $hr^{-1}$. In some embodiments, the uptake rate is at least about 20.7 mmol $gDW^{-1}$ $hr^{-1}$. In some embodiments, the uptake rate is at least about 43.1 mmol $gDW^{-1}$ $hr^{-1}$. In some embodiments, the substrate for uptake is glucose. In some embodiments, D-lactate is produced from the glucose.

In some embodiments, a strain is provided having a production rate of at least about 30 mmol per grams dry weight per hour (mmol $gDW^{-1}$ $hr^{-1}$) under standard conditions in 1 g per liter yeast extract medium, for example about 30 mmol $gDW^{-1}$ $hr^{-1}$, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190 or 200 mmol $gDW^{-1}$ $hr^{-1}$, including ranges between any two of the listed values. In some embodiments, the strain may provide more than 200 mmol $gDW^{-1}$ $hr^{-1}$. In some embodiments, the substrate is glucose and the product is D-lactate. In some embodiments, the glucose uptake rate is 18 mmol $gDW^{-1}$ $hr^{-1}$ and minimal medium conditions are used.

In some embodiments, a strain is provided having a growth rate of at least about 0.2 $hr^{-1}$ is provided, for example a growth rate of about 0.2 $hr^{-1}$, 0.25, 0.26, 0.3, 0.35, 0.4, 0.45, 0.5, 0.55, 0.6, 0.65, 0.7, 0.75, 0.8, 0.85, 0.86, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, or 2 $hr^{-1}$, including ranges between any two of the listed values. In some embodiments, a strain having a growth rate of more than 2 $hr^{-1}$ is provided.

Additional Alternative Embodiments

Traditional metabolic engineering can require a high level of organism familiarity and biological intuition. However, with systems biology methods and genome-scale metabolic models, it is possible to reliably and systematically predict the phenotype of microbial organisms (Park et al. 2008). Successful cases of systems biology driven strain designs for *E. coli* include production of the metabolites lycopene (Alper et al. 2005a; Alper et al. 2005b), lactic acid (Fong et al. 2005), succinic acid (Lee et al. 2005; Lee et al. 2008; Wang et al. 2006), and amino acids (Lee et al. 2007; Park et al. 2007). These cases demonstrated in *E. coli* as well as those for additional organisms have been reviewed (Feist and Palsson 2008; Park et al. 2008) and represent examples of metabolic engineering driven by systems biology.

Although lactate production strains have been constructed previously (Chang et al. 1999; Dien et al. 2001; Zhou et al. 2003; Zhu et al. 2007), strains according to some embodiments herein can differ in one or more of the following aspects: (i) strains according to some embodiments herein can be generated without any recombinant DNA, thus streamlining the construction and fermentation process (e.g., no induction of a transgene is required), (ii) strains according to some embodiments herein do not require complex fermentations, such as two-stage aerobic and anaerobic fermentations; (iii.) strains according to some embodiments herein have the potential for continuous processing.

Model-driven design also has an advantage in that it offers a means to quickly predict the effect of additional knockouts and supplementation of medium, which was mostly speculative and performed by trial and error in other studies. One specific prediction from modeling was that acetyl-CoA could be generated in the pflABfocA, pflDC, aceEF knockout strain through pathways detailed in the model that were previously speculated not to be utilized (Zhu et al. 2007). The weaning of the strain off of acetate supplementation provides evidence that this is indeed possible; however the necessity of yeast extract for continued growth indicates that further testing is needed. Modeling predicted that the lactate produced here is optically pure D-lactate, as the predicted active enzyme is that of the D-lactate specific ldhA gene. Optically pure lactate is preferred for polymer generation (Hofvendahl and Hahn-Hagerdal 2000) and can be directly assayed in these strains. The next step for the evaluation of this lactate producing strain is evolution under continuous processing conditions and higher substrate conditions. Strains that are growth coupled are, in theory, suitable for continuous culture as they will not be outperformed by mutants that exhibit faster growth under such conditions. This continuous processing potential may significantly impact the field of metabolic engineering.

EXAMPLES

Example 1: Computational Model and in Silico Design

The metabolic reconstruction of *E. coli* iAF1260 (Feist et al. 2007) with the minor changes described (Feist et al. 2010) was utilized. This model has been functionally tested and verified against experimental data to accurately predict growth rates, metabolite excretion rates, and growth phenotypes on a number of substrate and genetic conditions (Feist et al. 2007). For all simulations, the reactions CAT, SPODM, and SPODMpp (oxidative stress reactions) and the FHL reaction were constrained to zero for reasons previously established (Feist et al. 2007). Flux balance analysis (Price et al. 2004) was used for computing optimal phenotypes using iAF1260 and the biomass objective function, BOF-CORE, with the reported maintenance energies presented with the reconstruction (Feist et al. 2007). All computations were performed using the MATLAB (The MathWorks Inc., Natick, Mass.) and the COBRA Toolbox (Becker et al. 2007) software packages with TOMLAB (Tomlab Optimization Inc., San Diego, Calif.) solvers.

Model conditions were set to computational minimal medium as previously defined (Feist et al. 2007). Minimal medium with yeast extract supplementation (for experimental comparison) was simulated by allowing amino acid and nucleotide base uptake rates for simulations in amounts proportional to that required for supporting a given experimentally determined growth rate computationally. In modeling terms, a given uptake rate for an amino acid or nucleotide base was equal to the stoichiometric coefficient of that component in the biomass objective function multiplied by the experimental growth rate. The growth and non-growth associated maintenance modeling parameters identified in model development for growth on glucose were used for all design calculations (Feist et al. 2007).

In order to improve computationally identified growth coupled knockout strains and reduce the number of knockouts necessary, a COBRA Toolbox function (Becker et al. 2007) called analyzeGCdesign (see Supplementary Files) was created. This function uses a simple algorithm and objective function to find a better growth coupled solution, given an OptKnock or OptGene solution (or any set of knockouts) as an input (Feist et al. 2010).

Example 2: Selection of Strain Designs

From the pool of computational designs (Feist et al. 2010), the production of D-lactate from glucose was identified as a production target as lactate was predicted to be a homofermentation product with a high yield. The original designs generated from the computational analysis gave two designs for three- and five-reaction knockouts that could result in the high yield phenotype (Table I). A sensitivity analysis using the analyzeGCdesign algorithm with a penalty for knockouts of 90% was performed on each of the designs to determine if the high yield could be sustained or improved with fewer metabolic interventions (i.e., knockouts). This analysis returned a two reaction removal design (reactions PFL, pyruvate formate lyase, and PDH, pyruvate dehydrogenase) as the optimal design for the given knockout penalty and maximization of yield starting from the three knockout design, and a single reaction removal (ALCD2x, alcohol dehydrogenase (ethanol)) starting from the five knockout design. The PFL and PDH design for the production of lactic acid from glucose was found to be a novel design based on a literature search, although similar designs exist (Zhou et al. 2003; Zhu et al. 2007), and it was selected for construction.

TABLE I

Results of computational analysis of strain designs for production of D-lactate from glucose.

| OptKnock Design | Production Rate (mmol gDW$^{-1}$ hr$^{-1}$) | Yield (wt %) | By-products | By-product Rate (mmol gDW$^{-1}$ hr$^{-1}$) | By-product Yield (wt %) | Growth Rate (hr$^{-1}$) | analyzeGC design Max Yield - 90% KO Penalty |
|---|---|---|---|---|---|---|---|
| PDH, PFL, PGI | 36.158 | 90.4% | succinate CO$_2$ | 0.087 0.51 | 0.3% 0.6% | 0.261 | PFL, PDH |

TABLE I-continued

Results of computational analysis of strain designs for production of D-lactate from glucose.

| OptKnock Design | Production Rate (mmol gDW$^{-1}$ hr$^{-1}$) | Yield (wt %) | By-products | By-product Rate (mmol gDW$^{-1}$ hr$^{-1}$) | By-product Yield (wt %) | Growth Rate (hr$^{-1}$) | analyzeGC design Max Yield - 90% KO Penalty |
|---|---|---|---|---|---|---|---|
| ALCD2x, ATPS4rpp, G6PDH2r, GHMT2r, PGI | 38.429 | 96.1% | acetate succinate CO$_2$ | 0.138 0.033 0.196 | 0.2% 0.1% 0.2% | 0.100 | ALCD2x |

Example 3: Strain Construction

The starting strain was wild-type *E. coli* K-12 MG1655 (ATCC 700926). This strain has been extensively characterized physiologically (Fong et al. 2005; Fong et al. 2003; Ibarra et al. 2002; Reed et al. 2006), and its genome has been resequenced (Herring et al. 2006. Nat Genet. 38(12):1406-1412, hereby incorporated by reference in its entirety). A genomic sequence of wild-type *E. coli* K-12 MG1655 is provided as SEQ ID NO: 1. The computational model iAF1260 is based on the K-12 MG1655 genome. Gene disruptions were performed using homologous recombination of PCR-amplified linear fragments (Datsenko and Wanner 2000). During the gene deletion process, strains were grown aerobically in LB liquid medium and on 1.0% agar plates and the antibiotics kanamycin, chloramphenicol, and ampicillin were used for section. The plasmids pKD46, pKD13, and pCP20 were used in this process. Strains were preserved at −80° C. and were given a systematic "BOP" tag and number (for example, BOP27) under a standard strain identifier protocol. Knockout genotypes were confirmed by PCR using pairs of locus-specific primers.

Three operons were removed to completely eliminate the activity of the two reactions in the design. Two operons for the PFL reaction, pflABfocA, the main isozyme and additionally the transporter that allows passage of the reaction by-product formate, and pflDC, the minor isozyme. Removal of one operon, aceEF, encoding the core of the pyruvate dehydrogenase catalyzing enzyme, eliminated the PDH reaction. These gene deletions were defined in the gene to protein to reaction associations in iAF1260 (Feist et al. 2007). The resultant strain was labeled BOP338 (Table II). The operons xylFGH, rbsACB, and alsBAC were also deleted in order to improve the strain's ability to grow on xylose, although it was only grown on glucose in this study. This strain was labeled BOP374 (Table II).

TABLE II

Strains according to some embodiments herein (SS—steady-state evolution, SPE—serial passage exponential)

| Strain | Parent | Evolution | Genotype |
|---|---|---|---|
| BOP27 | N/A | | MG1655 ATCC#47076 |
| BOP330 | BOP27 | | pflABfocA kan + |
| BOP336 | BOP331 | | pflABfocA pflDC kan + |
| BOP338 | BOP337 | | pflABfocA pflDC aceEF kan + |
| BOP370 | BOP339 | | pflABfocA pflDC aceEF xylFGH kan + |
| BOP372 | BOP371 | | pflABfocA pflDC aceEF xylFGH rbsACB kan + |
| BOP374 | BOP372 | | pflABfocA pflDC aceEF xylFGH rbsACB alsBAC kan + |
| BOP374e | BOP374 | SS, 16 days | pflABfocA pflDC aceEF xylFGH rbsACB alsBAC kan + |
| BOP384 | BOP374e | | pflABfocA pflDC aceEF xylFGH rbsACB alsBAC mutS kan + |
| BOP384eG1 | BOP384 | SPE, 14 days | pflABfocA pflDC aceEF xylFGH rbsACB alsBAC mutS kan + |
| BOP384eG2 | BOP384 | SPE, 14 days | pflABfocA pflDC aceEF xylFGH rbsACB alsBAC mutS kan + |

After construction of the production strain, it was analyzed for growth properties under the minimal medium conditions for which it was designed to be evolved and optimized in. Minimal media for cultures was selected as follows: M9 minimal was selected as it has been demonstrated that lactic acid can be made with the given defined minimal nutrients (Fong et al. 2005). Yeast extract (Sigma, Catalog #8013-01-2) and sodium acetate were used as supplementation where specified. This analysis was done in batch mode and the results are shown in Table III. The screen revealed that the lactate production strain constructed was auxotrophic for acetate. This indicates that the strain was not able to make the necessary acetyl-CoA required for generation of lipids. With the strain containing PFL and PDH knockouts, this result was not unexpected. These growth rates could potentially increase with adaptation to these conditions. Furthermore, supplementation with yeast extract, a widely used culture supplement (see below) also increased the growth rate in a few instances examined, but could not support growth as the only supplement along with glucose (data not shown).

TABLE III

Initial growth characteristics of production strains (NG—no growth)

| Strain | Culture Conditions | Supplement | Aerobicity | Growth Rate (hr$^{-1}$) |
|---|---|---|---|---|
| BOP338 | 4 g/L glucose M9 | none | aerobic | NG |
| BOP338 | 4 g/L glucose M9 | 1 g/L acetate | aerobic | 0.37 |
| BOP374 | 4 g/L glucose M9 | none | aerobic | NG |
| BOP374 | 4 g/L glucose M9 | 1 g/L acetate | aerobic | 0.43 |
| BOP374 | 4 g/L glucose M9 | none | anaerobic | NG |
| BOP374 | 4 g/L glucose M9 | 1 g/L acetate | anaerobic | 0.16 |

Examples 4-5

Continuous Culture Evolutions

Continuous culture was performed in a 1.0 L New Brunswick BioFlo fermentor. M9 medium was used in the fermentor as specified. The agitation rate was 500 RPM and was constant for the run. Temperature was maintained at 37° C. Culture pH was maintained with 5% NaOH and was maintained at 7.0. Dissolved oxygen was also monitored for the evolution and was maintained at zero. The volume of medium in the fermentor was maintained at 1.0 L unless noted otherwise. To maintain anoxic conditions in the fermentor, 5% CO2 balance $N_2$ gas was supplied to the fermentor at 1 VVM. For the weaning off of acetate, the glucose concentration was 4.0 g/L and the acetate was at 2.0 g/L. Feed rates are presented in the results section as a function of time. Samples were removed aseptically and optical density measurements were taken. Samples were analyzed by HPLC.

Products were identified and quantified by HPLC using an Aminex 87-H ion exchange column at 65° C. The mobile phase was 5 mM H2SO4 at an isocratic flow of 0.5 mL/minute. Sample injection volume was 10 μL. Products were identified by retention time using utilizing ultraviolet detection at 210 nm and refractive index detection at 30° C. internal temperature and 45° C. external temperature and quantified by relating peak area to those of standards.

Adaptive evolution was conducted in 100 mL flasks with M9 medium supplemented with 4.0 g/L glucose. Other supplements are stated in the Results section. Cultures were maintained at 37° C. in an anaerobic chamber with the atmospheric gas being a mixture of 7.5% H2/10% CO2 with balance $N_2$. Experiments were designed to keep cells growing in exponential growth phase. To do this, the inoculum volume was changed for each passage throughout the course of evolution, and passages were performed at an optical density of approximately 0.2. Cultures were frozen and stored at −80° C. at regular intervals throughout adaptive evolution, approximately every other day.

Example 4: Adaptive Evolution to Alleviate Acetate Auxotrophy

Figure 2:
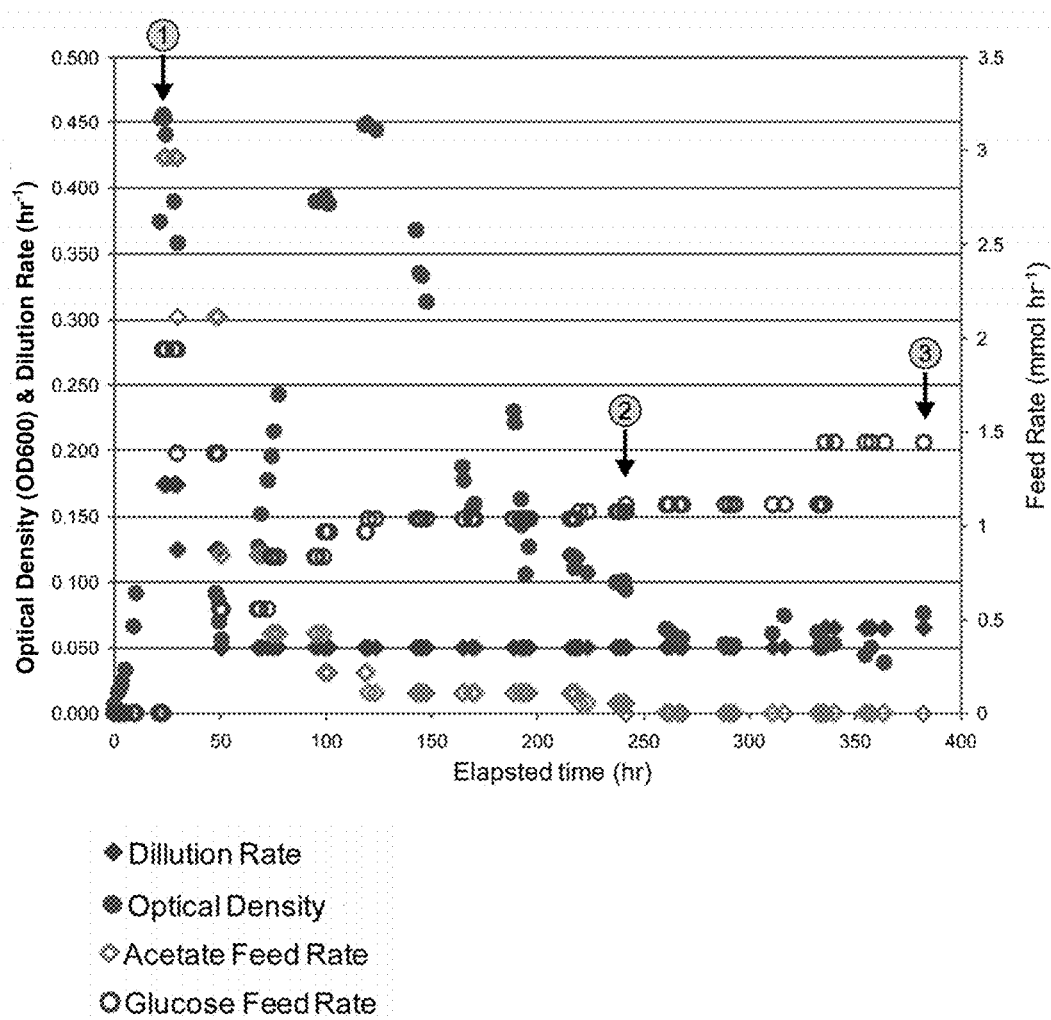
FIG. 2 is a graph illustrating continuous culture adaptive evolution of strain BOP374 to remove acetate auxotrophy according to some embodiments herein. Three different time points are denoted, (1) the time at which continuous culture was initiated, (2) the point at which acetate feed to the culture was ended, and (3) the time at which a strain was collected. The dilution rate (hr$^{-1}$), optical density (OD600), and feed rates for glucose and acetate (mmol hr$^{-1}$) are given. As the acetate feed was decreased, the cellular density decreased. At point 3, the evolution resulted in isolation of a strain that could grow solely on glucose.

Adaptive evolution was also used to alleviate the acetate auxotrophy. BOP374 was evolved in a 1.0 L chemostat anaerobically with a stepwise decreasing acetate feed rate (FIG. 2). To do this, the strain was initially inoculated into the fermentor in a batch mode with a glucose and acetate mixture, after the culture grew up to an appreciable density (point 1), the culture was run in continuous culture mode for 16 days, during which the acetate feed rate was sequentially lowered until the strain was growing solely on glucose minimal medium (point 2). At the end of the evolution, a colony was isolated from the fermentor and was designated and preserved with a new strain number (point 3). Continuous culture was chosen for the evolution as it allowed for automation and monitoring of the process along with a straightforward procedure to drop auxotrophy feed rates. The evolved strain harvested at the end of the evolution was confirmed to have the same genotype as the starting strain (in terms of gene knockouts) and was designated BOP374e.

Example 5: Adaptive Evolution to Optimize Production Phenotypes

In order to increase the rate of mutation and subsequently reduce the time necessary to evolve strains to an optimal phenotype, the mutS gene was removed from strain BOP374e to generate the mutator strain BOP384 (Table II). The mutS gene is involved in DNA mismatch repair (Acharya et al. 2003; Schlensog and Bock 1991), thus its removal can cause a substantial increase in the mutation rate of E. coli (Giraud et al. 2001; Shaver et al. 2002).

Figure 3:
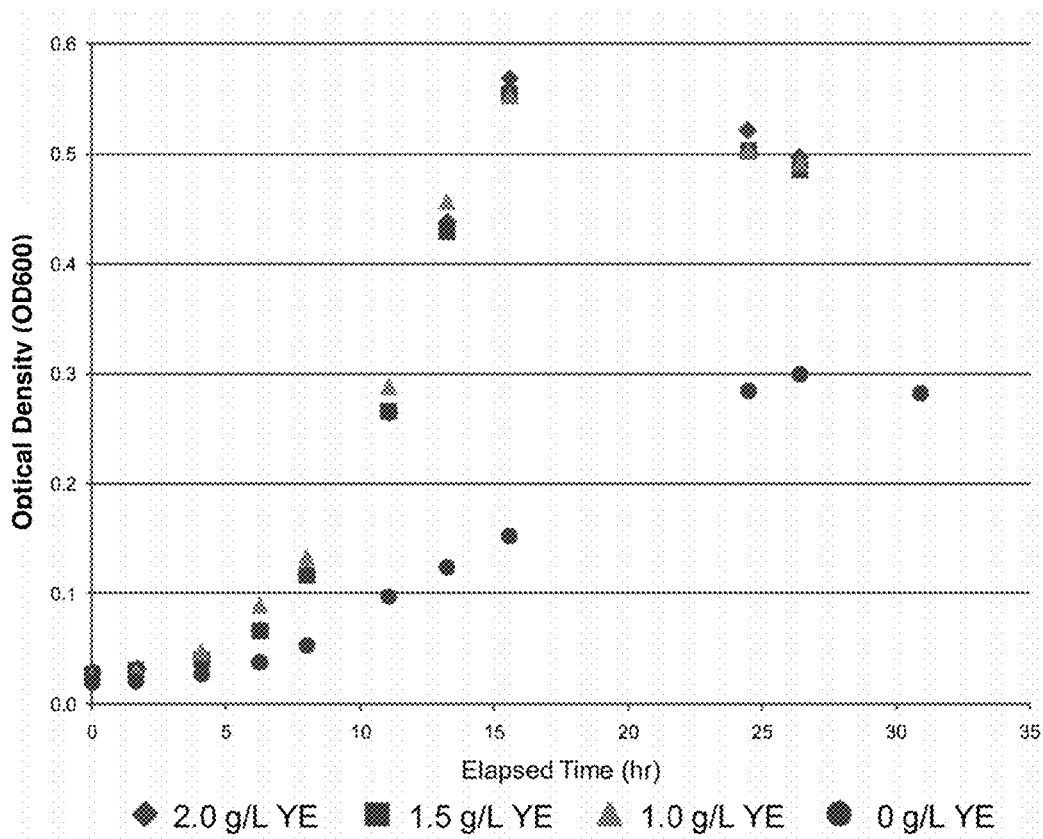
FIG. 3 is a graph illustrating growth characteristics of microbial cells according to some embodiments herein. BOP384, the lactate production strain was examined for its growth on glucose minimal medium with and without supplementation of yeast extract (YE) at different levels. All levels of supplementation had a similar growth profile and final optical density, both greater than those for no supplementation.
Figure 4:
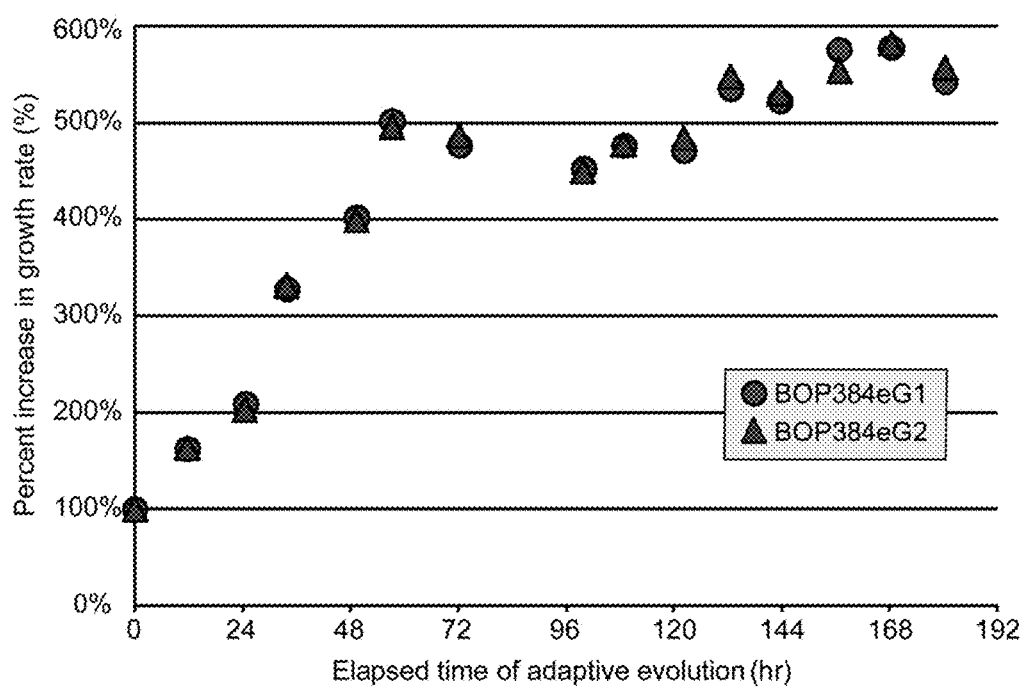
FIG. 4 is a graph illustrating the percent increase of growth rate by adaptively evolved strains according to some embodiments herein. Growth rate over an initial unevolved lactate production strain (e.g. strain BOP384) is shown over time for strains evolved on glucose. The strain was evolved in duplicate in parallel evolutions. The initial growth rates were determined each on glucose and the same starting strain was used for both evolutions. Both duplicates (BOP384eG1 and BOP384eG2) possessed a similar growth rate path to the end phenotype and similar final endpoint growth rates.

Initial characterization of the lactate production strain revealed that supplementation of the medium with yeast extract (YE) was necessary to sustain anaerobic growth during the adaptive evolution process. Strains growing with supplementation all possessed approximately the same growth profile and production characteristics when compared to the unsupplemented culture (FIG. 3). For the supplemented cultures, the maximum growth rate was 0.26±0.01 hr-1. The culture without supplementation had a maximum growth rate of 0.20 hr-1 during exponential phase. The overall batch product yields, Yp/s, are given in Table IV. After BOP384 growing with no supplementation was passed to fresh medium (with the same initial composition, no supplementation) under anaerobic conditions, growth ceased in numerous attempts after approximately two to three culture doublings (results not shown), further justifying the choice of medium supplementation with yeast extract BOP384 was evolved in duplicate on glucose using the established batch serial passage adaptive evolution process to keep the population in exponential growth phase (see Materials and Methods). The starting strain was unevolved BOP384 supplemented with 1.0 g/L YE (characteristics are shown in Table IV). Both of the duplicate evolutions resulted in endpoint strains with very similar growth and production profiles. The percent increase over the initial 0.26±0.01 hr-1 growth rate after the first 200 hours of the entire evolution (which was about 14 days total) was roughly 500%, as shown in FIG. 4. There was a rapid increase in the growth rate during the adaptation with the cultures reaching their final growth rates in about 2.5 days. This adaptation period of 2.5 days is much less than that of E. coli in other adaptive evolution experiments in which strains reached their final growth rate in 10-30 days (Fong and Palsson 2004; Ibarra et al. 2002). The final growth rate anaerobically was much higher than observed in earlier studies. In total, the evolution process was carried out for slightly over 14 days until the growth rate stopped increasing. Single colonies were isolated from the final cultures of each evolution (after 14 days), their knockout genotypes were confirmed by PCR, and they were designated as BOP384eG1 and BOP384eG2.

Strains BOP384eG1 and BOP384eG2 were cultured from frozen stocks and examined for their production capabilities. It is noted that the growth rates of the indicated populations are illustrated reported in FIG. 4, whereas clonal isolates are exampled and reported in Table IV. Furthermore, growth rates from FIG. 4 may include overestimates due to characteristic dilution error that can occur when calculating the expected small inoculation sizes. Nonetheless, the increase in growth phenotype is significant.

Example 6: Growth Rates, Culture Doublings, and Division Events of Engineered Microbial Strains Cell concentration in cultures was determined by measuring the optical density at 600 nm (OD600) using a Biomate 3 spectrophotometer (Thermo Scientific, USA). A value of 1.55*1012 cells L-10D600$^{-1}$ was used to calculate cell numbers with a dry cell weight of 2.9*10-13 gDW cell$^{-1}$ (Neidhardt 1996). Total biomass can be calculated as 0.45 gDW L$^{-1}$ OD600$^{-1}$. Growth rates of batch cultures during exponential growth were determined using at least three cell and metabolite concentration data points.

The mutations that accumulate during adaptive evolution occur randomly during cell division, so it was useful to calculate the total number of cell doublings that have occurred at any time. The formula used for this was D=($2^G$−1)*I where D is the total number of cellular division events, I is the initial number of cells, and G is the number of cell divisions per initial cell (the number of generations). One doubling occurred for every new cell in the culture.

Characterization of the final lactate producing strains indicated evolution to a production phenotype in agreement with computational predictions. Table IV contains data from the characterization of the endpoint strains. The final production rate of lactate was 84.4±1.5 mmol gDW$^{-1}$ hr$^{-1}$ and additionally succinate was made a rate of 4.3±0.3 mmol gDW$^{-1}$ hr$^{-1}$. This correlated to a 97.9±1.2% and 6.5±0.3% wt % product yield at steady-state during the exponential growth phase for lactate and succinate, respectively. Overall percent product yields for lactate and succinate were 98.4±3.4% and 3.4±2.8% wt %, respectively. The overall yield was monitored throughout the evolution and was consistent at these values after 2.5 days of evolution. The steady-state production rate of lactate increased over 2 fold for the endpoint strain compared to the unevolved strain. The glucose consumption rate also has a similar 2 fold increase, and the production rate of succinate increased 7 fold. The steady-state wt % yield for lactate was approximately the same and that of succinate increased approximately 3.5 fold. The overall wt % yields were approximately the same for both lactate and succinate. The summation of the wt % yields over 100% indicate that some of the supplemented yeast extract was contributing to the lactate and/or succinate production. Overall, 93.8% of the total product generated during fermentation at steady-state was lactate, close to the homofermentative criteria set for the strain in the computational selection of strain designs.

Figure 5:
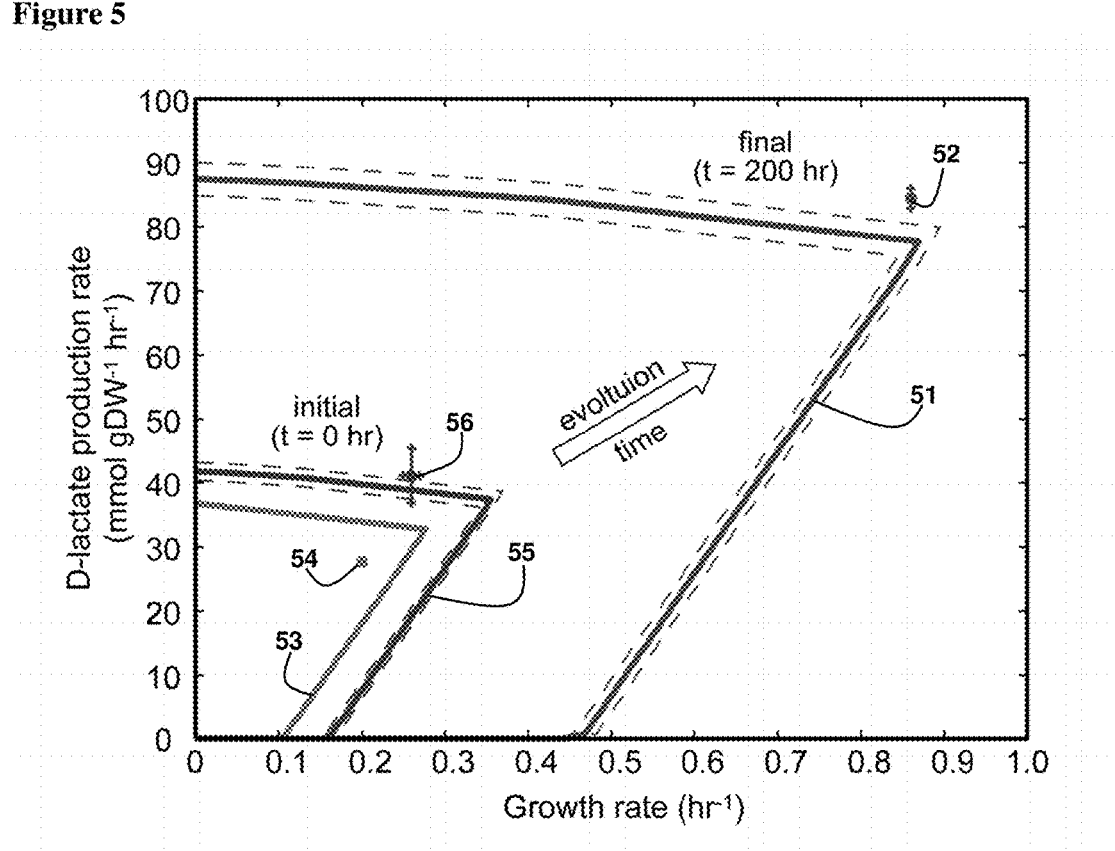
FIG. 5 is a graph illustrating the predicted production envelopes and experimental production measurements for unevolved and end point lactate production strains (BOP384, BOP384eG1, and BOP384eG2). The production envelopes are given based on experimentally measured substrate uptake rates (mmol gDW$^{-1}$ hr$^{-1}$), solid lines (averages) and dashed lines (considering standard deviation). Also plotted are the experimentally measured values for the lactate production rates (mmol gDW$^{-1}$ hr$^{-1}$) and growth rates (hr$^{-1}$). Experimental values are given in Table IV. The line 51 and point 52 are for the endpoint strain (with error bars); line 53 is the unevolved strain without supplementation (single measurement 54); and line 55 and point 56 are for the unevolved strain with yeast extract supplementation. For the endpoint, the optimal growth rate value for the envelopes lies near the experimentally determined endpoint growth rate and lactate production rate. The evolution resulted in a significant increase in production and growth rates.

The data from the unevolved and evolved strains (including strains according to some embodiments herein) on glucose analyzed with the iAF1260 model is shown in FIG. 5. The computational predictions and experimentally evolved endpoint measurements display good agreement. For the measurement of unevolved, unsupplemented growth on glucose, the initial phenotype is suboptimal with the production rate and growth rate less than the optimally predicted point. Coincidentally, the glucose uptake rate of 18.4 is almost identical to that observed for anaerobic growth of E. coli in an earlier modeling and experimental evaluation of growth (Varma and Palsson 1994) and gives confidence in the single measurement. Supplementation with yeast extract for unevolved glucose growth displays near optimal behavior as predicted with the model at the measured uptake rate. This demonstrates that yeast extract allows more incoming carbon (glucose and yeast extract content) to be used for lactate production and for biomass generation. The endpoint predictions and experimental measurements are in good agreement, with the experimentally measured growth rate and lactate production rate contributing to a point very near the optimal growth rate. The increased growth and production rates are due to the over 2 fold increase in the glucose uptake rate. This characterization of an adaptively evolved production strain demonstrates that a computationally designed strain can result in an experimentally verified production phenotype in good agreement with modeling predictions.

The endpoint strains (see Table IV and FIG. 5) display superior performance in terms of production rate, growth rate, and by-product formation over previously generated lactate production strains (Fong et al. 2005). In comparison to lactate production studies on an industrial scale, the steady-state and overall yields generated in this study of 0.98 g g$^{-1}$ are at the same level or above previously reported values of 0.9 g g$^{-1}$ (Chang et al. 1999), 0.93 g g$^{-1}$ (Dien et al. 2001), 1.0 g g$^{-1}$ (Zhou et al. 2003), and 0.86 g g$^{-1}$ (Zhu et al. 2007). Furthermore, even at the relatively low cellular densities used for this process, a volumetric productivity of 1.7 g L$^{-1}$ hr$^{-1}$ was achieved, comparing favorably with previous studies where cell densities were driven roughly an order of magnitude higher and productivity values of 0.7-3.5 g L$^{-1}$ hr$^{-1}$ were reported (Chang et al. 1999; Dien et al. 2001; Zhou et al. 2003; Zhu et al. 2007). The overall product yield is very close to theoretical maximum for a growing strain (Feist et al. 2010), and is even above the theoretical value when considering supplementation.

TABLE IV

Characterization of the lactate production strain BOP384 prior to and after evolution (% $Y_{p/s}$—percent production yield, Supp.—supplement, YE—yeast extract).

| Evolution Status | Supp. | Growth Rate (hr$^{-1}$) | Product/ Substrate | Production/ Consumption Rate (mmol gDW$^{-1}$ hr$^{-1}$) | % $Y_{p/s}$ Steady-State (wt %) | % $Y_{p/s}$ (wt %) |
|---|---|---|---|---|---|---|
| unevolved | 1, 1.5, 2 g/L YE | 0.26 ± 0.01 | glucose | 20.7 ± 0.7 | | |
| | | | lactate | 41.1 ± 4.2 | 99.7 ± 0.1% | 101.3 ± 6.4% |
| | | | succinate | 0.6 ± 0.1 | 1.8 ± 0.4% | 3.7 ± 0.5% |
| unevolved | none | 0.2 | glucose | 18.4 | | |
| | | | lactate | 27.7 | 75.30% | 97.30% |
| | | | succinate | 0 | 0% | 3.90% |
| evolved | 1 g/L YE | 0.86 ± 0.00 | glucose | 43.1 ± 1.3 | | |
| | | | lactate | 84.4 ± 1.5 | 97.9 ± 1.2% | *98.4 ± 3.4% |
| | | | succinate | 4.3 ± 0.3 | 6.5 ± 0.3% | *3.4 ± 2.8% |

*Overall yield monitored throughout evolution and was consistent after 2.5 days.

Example 7: Genomic Sequencing of Selected Microbial Strains

Clonal isolates of each of the strains indicated in Table V were taken along the course of the roughly 14 day evolution, sequenced, and compared to the wild type and starting strains. The following is a list of isolates which were sequenced:

TABLE V

Strains selected for sequencing
Strain selected for sequencing
(timepoint in evolution is indicated, if applicable)

'BOP27'-Wild Type-ATCC 700926
'BOP384' Day 0
'BOP384G1D' Day 3
'BOP384G1H' Day 5
'BOP384G1N' Day 8
'BOP384G1S' Day 10
'BOP384G1X' Day 13
'BOP384eG1' isolate 1 Day 14
'BOP384eG1' isolate 2 Day 14

Genomic DNA was isolated using Promega's Wizard DNA Purification Kit. The quality of DNA was assessed with UV absorbance ratios using a Nano drop. DNA was quantified using Qubit dsDNA High Sensitivity assay. Paired-end resequencing libraries were generated using Illumina's Nextera XT kit with 1 ng of input DNA total. The sequencing results were analyzed using the breseq analysis software.

Sequences of each strain that was sequenced were compared to a wild-type reference sequence, SEQ ID NO: 1. Mutations identified in the analysis, including the affected gene, if any, and the affected protein, if any, are shown in Table VIa. The mutations identified in each sequenced strain (recovered at various timepoints) and the location of the mutations are shown in Tables VIb and VIc in which "TRUE" indicates the presence of a mutation in a particular strain and a "blank" entry indicates that the wildtype sequence is present at that location in a particular strain. Thus, from Tables VIb and VIc, the complete genomic sequence of each strain may be determined. The mutations found in each of the following strains are annotated in SEQ ID NOs: 2-9, as indicated in Tables VIb and VIc.: BOP384' Day 0 (see SEQ ID NO: 2), BOP384G1D' Day 3 (see SEQ ID NO: 3), BOP384G1H' Day 5 (see SEQ ID NO: 4), BOP384G1N' Day 8 (see SEQ ID NO: 5), BOP384G1S' Day 10 (see SEQ ID NO: 6), BOP384G1X' Day 13 (see SEQ ID NO: 7), BOP384eG1' (isolate 1) Day 14 (see SEQ ID NO: 8), or BOP384eG1' (isolate 2) Day 14 (see SEQ ID NO: 9).

TABLE VIa

Mutations Identified from Genomic Sequencing

| Mutation Position & Nucleotide change (with reference to SEQ ID NO: 1) | Gene | Protein change |
| --- | --- | --- |
| 1022011 C→T | yccS | A366T (GCT→ACT) |
| 111897 G→A | yacF | Q235* (CAG→TAG) |
| 1135244 A→G | flgH | D153G (GAC→GGC) |
| 1137595 A→G | flgJ/flgK | intergenic (+60/-6) |
| 1163111 A→G | thiK | H210R (CAC→CGC) |
| 1247873 G→A | dhaM | A155A (GCC→GCT) |
| 1260197 C→T | prs | R301H (CGT→CAT) |
| 1274794 T→C | narL | S87G (AGC→GGC) |
| 1386732 A→G | tpx | L35P (CTG→CCG) |
| 1435247 Δ1 bp | micC | intergenic (-330/+37) |
| 1440978 G→A | ldhA/ydbH | intergenic (-111/-97) |
| 1580390 A→G | ydeN | S53S (AGT→AGC) |
| 1604028 T→C | lsrB | G318G (GGT→GGC) |
| 1610530 + C | yneH | coding (746/927 nt) |
| 1679479 T→C | folM | D160D (GAT→GAC) |
| 1682336 A→G | tus | E18E (GAA→GAG) |
| 1729483 G→A | lhr | P791P (CCG→CCA) |
| 1760136 G→A | sufC | P134L (CCG→CTG) |
| 1866695 G→A | yeaG | M588I (ATG→ATA) |
| 1929016 G→A | purT | M38M (GTG→ATG) |
| 1950262 G→A | yecE/yecN | intergenic (+25/-28) |

TABLE VIa-continued

Mutations Identified from Genomic Sequencing

| Mutation Position & Nucleotide change (with reference to SEQ ID NO: 1) | Gene | Protein change |
|---|---|---|
| 1976527 Δ776 bp | flhD/insB-5 | |
| 2071288 G→A | flu | D576N (GAT→AAT) |
| 2085304 + G | yoeI/yeeY | intergenic (-166/+49) |
| 2098010 T→C | gnd | Y428C (TAC→TGC) |
| 2257220 A→G | pscK | G33G (GGT→GGC) |
| 2358479 + C | yfaW | coding (958/1206 nt) |
| 2405257 G→C | lrhA/yfbQ | intergenic (-594/-326) |
| 2534334 Δ1 :: IS186 (-) + 6 bp :: Δ1 | crr | coding (479-484/510 nt) |
| 2620968 Δ1 bp | purN/ppk | intergenic (+74/-98) |
| 2662540 T→C | yfhR | G43G (GGT→GGC) |
| 2732557 + C | yfiH | coding (500/732 nt) |
| 2740321 T→C | yfiR | V142A (GTC→GCC) |
| 2763809 + C | yfjM/rnlA | intergenic (-11/-131) |
| 2767188 G→A | yfjQ | D168N (GAT→AAT) |
| 2782127 A→G | ypjB | pseudogene (907/1374 nt) |
| 2809146 + A | mpTRUE | coding (355/531 nt) |
| 2824039 T→C | srlA | G62G (GGT→GGC) |
| 2826646 G→A | gutM | V2M (GTA→ATA) |
| 2844070 G→A | hycE | P142S (CCG→TCG) |
| 2926442 + T | sdaC | coding (192/1290 nt) |
| 2927497 G→A | sdaC | G416D (GGT→GAT) |
| 2932138 T→A | fucA/fucP | intergenic (-428/-119) |
| 2965591 T→C | ptsP | N289S (AAC→AGC) |
| 2975919 T→C | lysA | T335A (ACC→GCC) |
| 3114125 C→T | yghJ | V1004M (GTC→ATC) |
| 3176882 G→A | tolC | R249H (CGC→CAC) |
| 3218853 T→C | ygjG | R446R (CGT→CGC) |
| 3246033 G→A | yqjA | S80N (AGC→AAC) |
| 3268091 C→T | yhaC/rnpB | intergenic (+467/+556) |
| 3268123 C→A | yhaC/rnpB | intergenic (+499/+524) |
| 3268165 C→T | yhaC/rnpB | intergenic (+541/+482) |
| 3279141 C→T | agaW/agaA | pseudogene (49/555 nt) |
| 3302829 Δ1 bp | mtr | coding (1011/1245 nt) |
| 3315496 A→G | nusA | L18P (CTA→CCA) |
| 3335733 C→T | mlaC | D61N (GAT→AAT) |
| 34111 + T | carB/caiF | intergenic (+73/-189) |

TABLE VIa-continued

Mutations Identified from Genomic Sequencing

| Mutation Position & Nucleotide change (with reference to SEQ ID NO: 1) | Gene | Protein change |
|---|---|---|
| 3429378 T→C | rimN | E20E (GAA→GAG) |
| 345189 A→G | yahN | Y125H (TAT→CAT) |
| 3506796 T→C | yhfW | H347R (CAC→CGC) |
| 3526004 T→C | yrfF | V505A (GTG→GCG) |
| 3548297 T→C | malP | K733K (AAA→AAG) |
| 379237 Δ1 bp | frmR/yaiO | intergenic (−132/+56) |
| 379237 Δ2 bp | frmR/yaiO | intergenic (−132/+55) |
| 386281 C→T | tauC | G29G (GGC→GGT) |
| 3955730 G→A | ilvY | R38R (CGC→CGT) |
| 3957957 C→T | ppiC/yifO | intergenic (−121/+78) |
| 3978813 C→A | rffM/yifK | intergenic (+94/−97) |
| 3982057 C→T | aslB | L359L (CTC→CTT) |
| 3983344 C→T | aslA | V229V (GTG→GTA) |
| 3990407 Δ8 bp | cyaA | coding (1232-1239/2547 nt) |
| 407943 A→G | ykiA | pseudogene (111/342 nt) |
| 4105271 A→G | fieF | A260A (GCA→GCG) |
| 4153541 A→G | argC | D173G (GAC→GGC) |
| 42111 C→A | caiT/fixA | intergenic (−180/−292) |
| 4234068 T→G | yjbE | V47G (GTC→GGC) |
| 4294403 + CG | gltP/yTRUEO | intergenic (+586/+56) |
| 4306572 3434 bp→82 bp | alsC | |
| 4444833 A→G | ytfN | D900G (GAT→GGT) |
| 4503718 G→A | yjhC | V137M (GTT→ATT) |
| 454725 C→T | tig | I123I (ATC→ATT) |
| 4604230 + G | leuP | noncoding (80/87 nt) |
| 4604346 Δ1 bp | leuQ | noncoding (79/87 nt) |
| 507894 T→C | ybaQ/copA | intergenic (+111/+205) |
| 533362 A→G | gcl | T75A (ACT→GCT) |
| 547694 A→G | ylbE_1 | pseudogene (139/252 nt) |
| 547831 + G | ylbE_1 | pseudogene (2/252 nt) |
| 558493 G→T | sfmC | L99L (CTG→CTT) |
| 560913 + G | sfmD | coding (1994/2604 nt) |
| 619171 A→G | fepC | G84G (GGT→GGC) |
| 653396 T→C | dpiA | Y104Y (TAT→TAC) |
| 696062 G→A | glnW/glnU | intergenic (−9/+26) |
| 700027 C→T | nagC | C264Y (TGC→TAC) |
| 700286 + C | nagC | coding (532/1221 nt) |

TABLE VIa-continued

Mutations Identified from Genomic Sequencing

| Mutation Position & Nucleotide change (with reference to SEQ ID NO: 1) | Gene | Protein change |
|---|---|---|
| 700599 + C | nagC | coding (219/1221 nt) |
| 700679 + G | nagC | coding (139/1221 nt) |
| 751964 C→T | ybgD | A19T (GCA→ACA) |
| 760544 C→T | sucA | C872C (TGC→TGT) |
| 844446 C→T | ybiO | P86P (CCG→CCA) |
| 852434 + A | mntR | coding (29/468 nt) |
| 922473 + G | clpS/clpA | intergenic (+17/−14) |
| 961467 C→T | rpsA | M84M (CTG→TTG) |
| 963462 A→G | ihfB/ycaI | intergenic (+127/−81) |

TABLE VIb

Mutations Identified from Genomic Sequencing

| Mutation Position & Nucleotide change | BOP27' (Wild Type) ATCC 700926 | BOP384' Day 0 (see SEQ ID NO: 2) | BOP384G1D' Day 3 (see SEQ ID NO: 3) | BOP384G1H' Day 5 (see SEQ ID NO: 4) | BOP384G1N' Day 8 (see SEQ ID NO: 5) |
|---|---|---|---|---|---|
| 1022011 C→T | | | TRUE | | |
| 111897 G→A | | | | | |
| 1135244 A→G | | | | | TRUE |
| 1137595 A→G | | | | | |
| 1163111 A→G | | | | | TRUE |
| 1247873 G→A | | | | TRUE | |
| 1260197 C→T | | | | | |
| 1274794 T→C | | | | | |
| 1386732 A→G | | | | | |
| 1435247 Δ1 bp | | | | | |
| 1440978 G→A | | | | | |
| 1580390 A→G | | | | TRUE | |
| 1604028 T→C | | | | | |
| 1610530 + C | | | | | TRUE |
| 1679479 T→C | | TRUE | | | |
| 1682336 A→G | | | | | |
| 1729483 G→A | | | | | |
| 1760136 G→A | | | TRUE | | |
| 1866695 G→A | | | | | |
| 1929016 G→A | | | TRUE | | |
| 1950262 G→A | | | | | TRUE |
| 1976527 Δ776 bp | | TRUE | TRUE | TRUE | TRUE |
| 2071288 G→A | | | | | |
| 2085304 + G | | | | | |
| 2098010 T→C | | | | | |
| 2257220 A→G | | | | | |
| 2358479 + C | | | | TRUE | |
| 2405257 G→C | | TRUE | TRUE | TRUE | TRUE |
| 2534334 Δ1 :: IS186 (—) + 6 bP :: Δ1 | | TRUE | TRUE | TRUE | TRUE |
| 2620968 Δ1 bp | | | | | |
| 2662540 T→C | | | | | TRUE |
| 2732557 + C | | | | | |
| 2740321 T→C | | TRUE | TRUE | TRUE | TRUE |
| 2763809 + C | | | | | |
| 2767188 G→A | | | | | |
| 2782127 A→G | | | | | |
| 2809146 + A | | | | | |
| 2824039 T→C | | | | | |
| 2826646 G→A | | | | | TRUE |
| 2844070 G→A | | | | | |

TABLE VIb-continued

Mutations Identified from Genomic Sequencing

| Mutation Position & Nucleotide change | BOP27' (Wild Type) ATCC 700926 | BOP384' Day 0 (see SEQ ID NO: 2) | BOP384G1D' Day 3 (see SEQ ID NO: 3) | BOP384G1H' Day 5 (see SEQ ID NO: 4) | BOP384G1N' Day 8 (see SEQ ID NO: 5) |
|---|---|---|---|---|---|
| 2926442 + T | | | | TRUE | |
| 2927497 G→A | | | | | TRUE |
| 2932138 T→A | | TRUE | TRUE | TRUE | TRUE |
| 2965591 T→C | | | | | |
| 2975919 T→C | | | | | |
| 3114125 C→T | | | | | |
| 3176882 G→A | | | | | |
| 3218853 T→C | | | | | |
| 3246033 G→A | | | | TRUE | |
| 3268091 C→T | | | | | |
| 3268123 C→A | | | | | |
| 3268165 C→T | | | | | |
| 3279141 C→T | | TRUE | TRUE | TRUE | TRUE |
| 3302829 Δ1 bp | | | | | |
| 3315496 A→G | | TRUE | | | |
| 3335733 C→T | | | | TRUE | |
| 34111 + T | | | | | TRUE |
| 3429378 T→C | | | TRUE | | |
| 345189 A→G | | | TRUE | | |
| 3506796 T→C | | | | | |
| 3526004 T→C | | | | | |
| 3548297 T→C | | | | TRUE | |
| 379237 Δ1 bp | | | | | TRUE |
| 379237 Δ2 bp | | | | | |
| 386281 C→T | | | | | |
| 3955730 G→A | | TRUE | | | |
| 3957957 C→T | TRUE | TRUE | TRUE | TRUE | TRUE |
| 3978813 C→A | | | | | |
| 3982057 C→T | | | | | |
| 3983344 C→T | | | | | |
| 3990407 Δ8 bp | | TRUE | TRUE | TRUE | TRUE |
| 407943 A→G | | | | | |
| 4105271 A→G | | | | | |
| 4153541 A→G | | TRUE | 0/47 | | |
| 42111 C→A | | | | | |
| 4234068 T→G | | | | | |
| 4294403 + CG | TRUE | TRUE | TRUE | TRUE | TRUE |
| 4306572 3434 bp→82 bp | | TRUE | TRUE | TRUE | TRUE |
| 4444833 A→G | | | | | |
| 4503718 G→A | | | | | |
| 454725 C→T | | | TRUE | TRUE | |
| 4604230 + G | | | | TRUE | |
| 4604346 Δ1 bp | | | | | |
| 507894 T→C | | TRUE | TRUE | TRUE | TRUE |
| 533362 A→G | | | | TRUE | |
| 547694 A→G | TRUE | TRUE | TRUE | TRUE | TRUE |
| 547831 + G | TRUE | TRUE | TRUE | TRUE | TRUE |
| 558493 G→T | | | | | |
| 560913 + G | | | | | |
| 619171 A→G | | | | | |
| 653396 T→C | | | | | |
| 696062 G→A | | | | | |
| 700027 C→T | | | | | TRUE |
| 700286 + C | | | | TRUE | |
| 700599 + C | | | | | |
| 700679 + G | | | TRUE | | |
| 751964 C→T | | TRUE | | | |
| 760544 C→T | | | | | |
| 844446 C→T | | | | | TRUE |
| 852434 + A | | | | TRUE | |
| 922473 + G | | | TRUE | | |
| 961467 C→T | | | | | |
| 963462 A→G | | | | | |

TABLE VIc

Mutations Identified from Genomic Sequencing

| Mutation Position & Nucleotide change | BOP384G1S' Day 10 (see SEQ ID NO: 6) | BOP384G1X' Day 13 (see SEQ ID NO: 7) | BOP384eG1' (isolate 1) Day 14 (see SEQ ID NO: 8) | BOP384eG1' (isolate 2) Day 14 (see SEQ ID NO: 9) |
|---|---|---|---|---|
| 1022011 C→T | | | | |
| 111897 G→A | | | TRUE | |
| 1135244 A→G | | | | |
| 1137595 A→G | | TRUE | TRUE | TRUE |
| 1163111 A→G | | | | |
| 1247873 G→A | | | | |
| 1260197 C→T | TRUE | | | |
| 1274794 T→C | | TRUE | TRUE | TRUE |
| 1386732 A→G | | | TRUE | |
| 1435247 Δ1 bp | | TRUE | | |
| 1440978 G→A | | TRUE | TRUE | TRUE |
| 1580390 A→G | | | | |
| 1604028 T→C | | TRUE | | |
| 1610530 + C | | | | |
| 1679479 T→C | | | | |
| 1682336 A→G | | TRUE | TRUE | TRUE |
| 1729483 G→A | | TRUE | TRUE | TRUE |
| 1760136 G→A | | | | |
| 1866695 G→A | | | TRUE | |
| 1929016 G→A | | | | |
| 1950262 G→A | TRUE | | | |
| 1976527 Δ776 bp | TRUE | TRUE | TRUE | TRUE |
| 2071288 G→A | | TRUE | TRUE | TRUE |
| 2085304 + G | | TRUE | TRUE | |
| 2098010 T→C | | TRUE | TRUE | TRUE |
| 2257220 A→G | | | TRUE | |
| 2358479 + C | | | | |
| 2405257 G→C | TRUE | TRUE | TRUE | TRUE |
| 2534334 Δ1::IS186 (—) + 6 bp::Δ1 | TRUE | TRUE | TRUE | TRUE |
| 2620968 Δ1 bp | TRUE | | | |
| 2662540 T→C | TRUE | | | |
| 2732557 + C | | TRUE | TRUE | |
| 2740321 T→C | TRUE | TRUE | TRUE | TRUE |
| 2763809 + C | TRUE | | | |
| 2767188 G→A | TRUE | | | |
| 2782127 A→G | | | TRUE | |
| 2809146 + A | | TRUE | TRUE | |
| 2824039 T→C | | | TRUE | |
| 2826646 G→A | TRUE | | | |
| 2844070 G→A | | TRUE | TRUE | TRUE |
| 2926442 + T | | | | |
| 2927497 G→A | TRUE | TRUE | TRUE | TRUE |
| 2932138 T→A | TRUE | TRUE | TRUE | TRUE |
| 2965591 T→C | | | TRUE | |
| 2975919 T→C | | TRUE | TRUE | TRUE |
| 3114125 C→T | TRUE | | | |
| 3176882 G→A | | | TRUE | |
| 3218853 T→C | TRUE | | | |
| 3246033 G→A | | | | |
| 3268091 C→T | TRUE | | | |
| 3268123 C→A | TRUE | | | |
| 3268165 C→T | TRUE | | | |
| 3279141 C→T | TRUE | TRUE | TRUE | TRUE |
| 3302829 Δ1 bp | TRUE | | | |
| 3315496 A→G | | | | |
| 3335733 C→T | | | | |
| 34111 + T | TRUE | TRUE | TRUE | |
| 3429378 T→C | | | | |
| 345189 A→G | | | | |
| 3506796 T→C | | | TRUE | |
| 3526004 T→C | | TRUE | TRUE | TRUE |
| 3548297 T→C | | | | |
| 379237 Δ1 bp | | TRUE | TRUE | |
| 379237 Δ2 bp | TRUE | | | |
| 386281 C→T | | TRUE | | TRUE |
| 3955730 G→A | | | | |
| 3957957 C→T | TRUE | TRUE | TRUE | TRUE |
| 3978813 C→A | | | TRUE | |
| 3982057 C→T | | TRUE | | |

TABLE VIc-continued

Mutations Identified from Genomic Sequencing

| Mutation Position & Nucleotide change | BOP384G1S' Day 10 (see SEQ ID NO: 6) | BOP384G1X' Day 13 (see SEQ ID NO: 7) | BOP384eG1' (isolate 1) Day 14 (see SEQ ID NO: 8) | BOP384eG1' (isolate 2) Day 14 (see SEQ ID NO: 9) |
|---|---|---|---|---|
| 3983344 C→T | TRUE | | | |
| 3990407 Δ8 bp | TRUE | TRUE | TRUE | TRUE |
| 407943 A→G | | TRUE | | |
| 4105271 A→G | | | TRUE | |
| 4153541 A→G | | | | |
| 42111 C→A | | | TRUE | |
| 4234068 T→G | TRUE | | | |
| 4294403 + CG | TRUE | TRUE | TRUE | TRUE |
| 4306572 3434 bp→82 bp | TRUE | TRUE | TRUE | TRUE |
| 4444833 A→G | | TRUE | TRUE | TRUE |
| 4503718 G→A | TRUE | | | |
| 454725 C→T | | | | |
| 4604230 + G | | | | |
| 4604346 Δ1 bp | | TRUE | | |
| 507894 T→C | TRUE | TRUE | TRUE | TRUE |
| 533362 A→G | | | | |
| 547694 A→G | TRUE | TRUE | TRUE | TRUE |
| 547831 + G | TRUE | TRUE | TRUE | TRUE |
| 558493 G→T | | | TRUE | |
| 560913 + G | | TRUE | TRUE | TRUE |
| 619171 A→G | | | TRUE | |
| 653396 T→C | | TRUE | TRUE | TRUE |
| 696062 G→A | | TRUE | | |
| 700027 C→T | | TRUE | TRUE | TRUE |
| 700286 + C | TRUE | | | |
| 700599 + C | | | | |
| 700679 + G | | | | |
| 751964 C→T | | | | |
| 760544 C→T | | TRUE | TRUE | TRUE |
| 844446 C→T | TRUE | | | |
| 852434 + A | | | TRUE | |
| 922473 + G | | | | |
| 961467 C→T | | | | |
| 963462 A→G | | | TRUE | |

General Comments

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

While the present invention has been described in some detail for purposes of clarity and understanding, one skilled in the art will appreciate that various changes in form and detail can be made without departing from the true scope of the invention.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

The foregoing description and Examples detail certain embodiments. It will be appreciated, however, that no matter how detailed the foregoing may appear in text, the invention may be practiced in many ways and the invention should be construed in accordance with the appended claims and any equivalents thereof.

REFERENCES

All references discussed herein, including the references below, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

Acharya S, Foster P L, Brooks P, Fishel R. 2003. The coordinated functions of the *E. coli* MutS and MutL proteins in mismatch repair. Mol Cell 12(1):233-46.

Alper H, Jin Y S, Moxley J F, Stephanopoulos G. 2005a. Identifying gene targets for the metabolic engineering of lycopene biosynthesis in *Escherichia coli*. Metab Eng 7(3):155-64.

Alper H, Miyaoku K, Stephanopoulos G. 2005b. Construction of lycopene-overproducing *E. coli* strains by combining systematic and combinatorial gene knockout targets. Nat Biotechnol 23(5):612-6.

Bailey J E. 1991. Toward a science of metabolic engineering. Science 252(5013):1668-75.

Becker S A, Feist A M, Mo M L, Hannum G, Palsson B O, Herrgard M J. 2007. Quantitative prediction of cellular metabolism with constraint-based models: The COBRA Toolbox. Nat. Protocols 2(3):727-738.

Burgard A P, Pharkya P, Maranas C D. 2003. Optknock: a bilevel programming framework for identifying gene knockout strategies for microbial strain optimization. Biotechnol Bioeng 84(6):647-57.

Chang D E, Jung H C, Rhee J S, Pan J G. 1999. Homofermentative production of D- or L-lactate in metabolically engineered *Escherichia coli* RR1. Appl Environ Microbiol 65(4):1384-9.

Datsenko K A, Wanner B L. 2000. One-step inactivation of chromosomal genes in *Escherichia coli* K-12 using PCR products. Proc Natl Acad Sci USA. 97(12):6640-5.

Dien B S, Nichols N N, Bothast R J. 2001. Recombinant *Escherichia coli* engineered for production of L-lactic acid from hexose and pentose sugars. J Ind Microbiol Biotechnol 27(4):259-64.

Feist A M, Henry C S, Reed J L, Krummenacker M, Joyce A R, Karp P D, Broadbelt L J, Hatzimanikatis V, Palsson B O. 2007. A genome-scale metabolic reconstruction for *Escherichia coli* K-12 MG1655 that accounts for 1260 ORFs and thermodynamic information. Mol Syst Biol 3(121).

Feist A M, Herrgard M J, Thiele I, Reed J L, Palsson B O. 2008a. Reconstruction of biochemical networks in microbial organisms. Nat Rev Microbiol Accepted.

Feist A M, Palsson B O. 2008. The growing scope of applications of genome-scale metabolic reconstructions using *Escherichia coli*. Nat Biotech 26(6):659-667.

Feist A M, Zielinski D C, Orth J D, Schellenberger J, Herrgard M J, Palsson B O. 2010. Model-driven evaluation of the production potential for growth-coupled products of *Escherichia coli*. Metab Eng. 12(3): 173-186.

Fong S S, Burgard A P, Herring C D, Knight E M, Blattner F R, Maranas C D, Palsson B O. 2005. In silico design and adaptive evolution of *Escherichia coli* for production of lactic acid. Biotechnol Bioeng 91(5):643-8.

Fong S S, Marciniak J Y, Palsson B O. 2003. Description and Interpretation of Adaptive Evolution of *Escherichia coli* K-12 MG1655 Using a Genome-scale in silico Metabolic Model. Journal of Bacteriology 185(21):6400-8.

Fong S S, Palsson B O. 2004. Metabolic gene-deletion strains of *Escherichia coli* evolve to computationally predicted growth phenotypes. Nat Genet. 36(10):1056-58.

Giraud A, Matic I, Tenaillon O, Clara A, Radman M, Fons M, Taddei F. 2001. Costs and benefits of high mutation rates: adaptive evolution of bacteria in the mouse gut. Science 291(5513):2606-8.

Herring C D, Raghunathan A, Honisch C, Patel T, Applebee M K, Joyce A R, Albert T J, Blattner F R, van den Boom D, Cantor C R and others. 2006. Comparative genome sequencing of *Escherichia coli* allows observation of bacterial evolution on a laboratory timescale. Nat Genet. 38(12):1406-1412.

Hofvendahl K, Hahn-Hagerdal B. 2000. Factors affecting the fermentative lactic acid production from renewable resources-1. Enzyme and Microbial Technology 26(2-4):87-107.

Ibarra R U, Edwards J S, Palsson B O. 2002. *Escherichia coli* K-12 undergoes adaptive evolution to achieve in silico predicted optimal growth. Nature 420(6912):186-9.

Lee K H, Park J H, Kim T Y, Kim H U, Lee S Y. 2007. Systems metabolic engineering of *Escherichia coli* for L-threonine production. Mol Syst Biol 3:149.

Lee S J, Lee D Y, Kim T Y, Kim B H, Lee J, Lee S Y. 2005. Metabolic engineering of *Escherichia coli* for enhanced production of succinic acid, based on genome comparison and in silico gene knockout simulation. Appl Environ Microbiol 71(12):7880-7.

Lee S Y, Kim J M, Song H, Lee J W, Kim T Y, Jang Y S. 2008. From genome sequence to integrated bioprocess for succinic acid production by Mannheimia succiniciproducens. Appl Microbiol Biotechnol 79(1):11-22.

Lee S Y, Papoutsakis E T. 1999. Metabolic Engineering: CRC Press.

Neidhardt F C, editor. 1996. *Escherichia coli* and *Salmonella*: cellular and molecular biology. 2nd ed. Washington, D.C.: ASM Press. 2 v. (xx, 2822, lxxvii) p.

Oh Y K, Palsson B O, Park S M, Schilling C H, Mahadevan R. 2007. Genome-scale reconstruction of metabolic network in *bacillus subtilis* based on high-throughput phenotyping and gene essentiality data. J Biol. Chem.

Park J H, Lee K H, Kim T Y, Lee S Y. 2007. Metabolic engineering of *Escherichia coli* for the production of L-valine based on transcriptome analysis and in silico gene knockout simulation. Proc Natl Acad Sci USA 104(19):7797-802.

Park J H, Lee S Y, Kim T Y, Kim H U. 2008. Application of systems biology for bioprocess development. Trends Biotechnol 26(8):404-12.

Patil K R, Rocha I, Forster J, Nielsen J. 2005. Evolutionary programming as a platform for in silico metabolic engineering. BMC Bioinformatics 6:308.

Price N D, Reed J L, Palsson B O. 2004. Genome-scale models of microbial cells: evaluating the consequences of constraints. Nat Rev Microbiol 2(11):886-897.

Reed J L, Patel T R, Chen K H, Joyce A R, Applebee M K, Herring C D, Bui O T, Knight E M, Fong S S, Palsson B O. 2006. Systems approach to refining genome annotation. Proc Natl Acad Sci USA 103(46):17480-4.

Schlensog V, Bock A. 1991. The *Escherichia coli* fdv gene probably encodes mutS and is located at minute 58.8 adjacent to the hyc-hyp gene cluster. J Bacteriol 173(23): 7414-5.

Shaver A C, Dombrowski P G, Sweeney J Y, Treis T, Zappala R M, Sniegowski P D. 2002. Fitness evolution and the rise of mutator alleles in experimental *Escherichia coli* populations. Genetics 162(2):557-66.

Stephanopoulos G, Nielsen J, Aristidou A. 1998. Metabolic Engineering. San Diego Academic Press.

Varma A, Palsson B O. 1994. Stoichiometric flux balance models quantitatively predict growth and metabolic by-product secretion in wild-type *Escherichia coli* W3110. Applied and Environmental Microbiology 60(10):3724-3731.

Wang Q, Chen X, Yang Y, Zhao X. 2006. Genome-scale in silico aided metabolic analysis and flux comparisons of *Escherichia coli* to improve succinate production. Appl Microbiol Biotechnol V73(4):887-894.

Zhou S, Causey T B, Hasona A, Shanmugam K T, Ingram L O. 2003. Production of Optically Pure D-Lactic Acid in Mineral Salts Medium by Metabolically Engineered *Escherichia coli* W3110. Appl. Environ. Microbiol. 69(1): 399-407.

Zhu Y, Eiteman M A, DeWitt K, Altman E. 2007. Homo-lactate fermentation by metabolically engineered *Escherichia coli* strains. Appl Environ Microbiol 73(2):456-64.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09932598B2). An electronic copy of the "Sequence Listing" will also be available from the USPTO upon request and payment of the fee set forth in 37 CFR 1.19(b)(3).

What is claimed is:

1. A genetically engineered recombinant *E. coli* comprising a genetic modification of pflABfocA and a genetic modification of pflDC which genetic modifications substantially reduce pyruvate formate lyase (PFL) activity, and a genetic modification which substantially reduces pyruvate dehydrogenase (PDH) activity, wherein the genetically engineered recombinant *E. coli* comprises a genotype of: pflABfocA pflDC aceEF xylFGH rbsACB alsBAC mutS.

2. The genetically engineered recombinant *E. coli* of claim 1, wherein the genetically engineered recombinant *E. coli* is configured for producing carbohydrates, wherein producing carbohydrates comprises producing D-lactate from a glucose precursor.

3. The genetically engineered recombinant *E. coli* of claim 1, wherein the genetic modifications which substantially reduce PFL activity reduce PFL activity by at least about 70%.

4. The genetically engineered recombinant *E. coli* of claim 1, wherein the genetic modification which substantially reduces PDH activity reduces PDH activity by at least about 70%.

5. The genetically engineered recombinant *E. coli* of claim 1, wherein the genetic modification which substantially reduces PFL activity reduces PFL activity by at least about 90%, and wherein the genetic modification which substantially reduces PDH activity reduces PDH activity by at least about 90%.

6. The genetically engineered recombinant *E. coli* of claim 1, wherein the genetic modifications which substantially reduce PFL activity eliminate PFL activity, and wherein the genetic modification which substantially reduces PDH activity eliminates PDH activity.

7. The genetically engineered recombinant *E. coli* of claim 1, wherein the genetically engineered recombinant *E. coli* has undergone adaptive evolution.

8. The genetically engineered recombinant *E. coli* of claim 1, further comprising a genetic modification that increases the mutation rate of the genetically engineered recombinant *E. coli* at least about 2-fold per generation.

9. The genetically engineered recombinant *E. coli* of claim 8, wherein the genetic modification that increases the mutation rate comprises a loss-of-function mutation in the mutS gene.

10. The genetically engineered recombinant *E. coli* of claim 1, wherein the genetic modifications which substantially reduce PFL activity are selected from the group consisting of: a hypomorphic mutation in each of pflABfocA and pflDC, a phenotypic null mutation in each of pflABfocA and pflDC, a deletion of each of pflABfocA and pflDC, a hypomorphic mutation in pflABfocA and a deletion of pflDC, a deletion of pflABfocA and a hypomorphic mutation in pflDC, a hypomorphic mutation in pflABfocA and a phenotypic null mutation in pflDC, a null mutation in pflABfocA and a hypomorphic mutation in pflDC, a deletion of in pflABfocA and a null mutation in pflDC, and a phenotypic null mutation in pflABfocA and a deletion of pflDC.

11. The genetically engineered recombinant *E. coli* of claim 1, wherein the genetic modification which substantially reduces PDH activity is selected from the group consisting of a hypomorphic mutation in aceEF, a null mutation in aceEF, and a deletion of aceEF.

12. The genetically engineered recombinant *E. coli* of claim 1, wherein the genetic modifications which substantially reduce PFL activity comprise a deletion of each of pflABfocA and pflDC, and wherein the genetic modification eliminating PDH activity comprises a deletion of aceEF.

13. The genetically engineered recombinant *E. coli* of claim 1, wherein the genetically engineered recombinant *E. coli* is of one of the BOP384eG1 strain or BOP384eG2 strain.

14. The genetically engineered recombinant *E. coli* of claim 1, further comprising deletion of each of a native xylGFH, rbsACB, and alsBAC operon.

15. The genetically engineered recombinant *E. coli* of claim 1, further comprising at least one mutation selected from the group consisting of: 1022011 C→T, 111897 G→A, 1135244 A→G, 1137595 A→G, 1163111 A→G, 1247873 G→A, 1260197 C→T, 1274794 T→C, 1386732 A→G, 1435247 Δ1 bp, 1440978 G→A, 1580390 A→G, 1604028 T→C, 1610530+C, 1679479 T→C, 1682336 A→G, 1729483 G→A, 1760136 G→A, 1866695 G→A, 1929016 G→A, 1950262 G→A, 1976527 Δ776 bp, 2071288 G→A, 2085304+G, 2098010 T→C, 2257220 A→G, 2358479+C, 2405257 G→C, 2534334 Δ1::IS186 (−)+6 bp::Δ1, 2620968 Δ1 bp, 2662540 T→C, 2732557+C, 2740321 T→C, 2763809+C, 2767188 G→A, 2782127 A→G, 2809146+A, 2824039 T→C, 2826646 G→A, 2844070 G→A, 2926442+T, 2927497 G→A, 2932138 T→A, 2965591 T→C, 2975919 T→C, 3114125 C→T, 3176882 G→A, 3218853 T→C, 3246033 G→A, 3268091 C→T, 3268123 C→A, 3268165 C→T, 3279141 C→T, 3302829 Δ1 bp, 3315496 A→G, 3335733 C→T, 34111+T, 3429378 T→C, 345189 A→G, 3506796 T→C, 3526004 T→C, 3548297 T→C, 379237 Δ1 bp, 379237 Δ2 bp, 386281 C→T, 3955730 G→A, 3957957 C→T, 3978813 C→A, 3982057 C→T, 3983344 C→T, 3990407 Δ8 bp, 407943 A→G, 4105271 A→G, 4153541 A→G, 42111 C→A, 4234068 T→G, 4294403+CG, 4306572 3434 bp→82 bp, 4444833 A→G, 4503718 G→A, 454725 C→T, 4604230+G, 4604346 Δ1 bp, 507894 T→C, 533362 A→G, 547694 A→G, 547831+G, 558493 G→T, 560913+G, 619171 A→G, 653396 T→C, 696062 G→A, 700027 C→T, 700286+C, 700599+C, 700679+G, 751964 C→T, 760544 C→T, 844446 C→T, 852434+A, 922473+G, 961467 C→T, and 963462 A→G, with reference to SEQ ID NO: 1.

16. The genetically engineered recombinant *E. coli* of claim 2, wherein the genetically engineered recombinant *E. coli* has a steady-state glucose uptake rate of at least about 30 mmol per gDW per hour under standard conditions in 1 g per liter yeast extract medium.

17. A genetically engineered, recombinant *E. coli* comprising a genetic modification of pflABfocA and a genetic modification of pflDC which genetic modifications reduce pyruvate formate lyase (PFL) activity, and a genetic modification which reduces pyruvate deghydrogenase (PDH) activity, wherein said genetically engineered recombinant *E. coli* has a steady-state glucose uptake rate of at least about 30 mmol per gDW per hour under standard conditions in 1 g per liter yeast extract medium, the genetically engineered recombinant *E. coli* further comprising at least one mutation selected from the group consisting of: 1022011 C→T, 111897 G→A, 1135244 A→*G, 1137595 A→G, 1163111 A→G, 1247873 G→A, 1260197 C→T, 1274794 T→C, 1386732 A→G, 1435247 Δ1 bp, 1440978 G→A, 1580390 A→G, 1604028 T→C, 1610530+C, 1682336 A→G, 1729483 G→A, 1760136 G→A, 1866695 G→A, 1929016 G→A, 1950262 G→A, 2071288 G→A, 2085304+G, 2098010 T→C, 2257220 A→G, 2358479+C, 2620968 Δ1 bp, 2662540 T→C, 2732557+C, 2763809+C, 2767188 G→A, 2782127 A→G, 2809146+A, 2824039 T→C, 2826646 G→A, 2844070 G→A, 2926442+T, 2927497 G→A, 2965591 T→C, 2975919 T→C, 3114125 C→T, 3176882 G→A, 3218853 T→C, 3246033 G→A, 3268091 C→T, 3268123 C→A, 3268165 C→T, 3302829 Δ1 bp, 3335733 C→T, 34111+T, 3429378 T→C, 345189 A→G, 3506796 T→C, 3526004 T→C, 3548297 T→C, 379237 Δ1 bp, 379237 Δ2 bp, 386281 C→T, 3978813 C→A, 3982057 C→T, 3983344 C→T, 407943 A→G, 4105271 A→G, 42111 C→A, 4234068 T→G, 4444833 A→G, 4503718 G→A, 454725 C→T, 4604230+G, 4604346 Δ1 bp, 533362 A→G, 558493 G→T, 560913+G, 619171 A→G, 653396 T→C, 696062 G→A, 700027 C→T, 700286+C, 700599+C, 700679+G, 760544 C→T, 844446 C→T, 852434+A, 922473+G, 961467 C→T and 963462 A→G, with reference to SEQ ID NO: 1.

18. A genetically engineered recombinant *E. coli* comprising a genetic modification of pflABfocA and a genetic modification of pflDC which genetic modifications substantially reduce pyruvate formate lyase (PFL) activity, and a genetic modification which substantially reduces pyruvate dehydrogenase (PDH) activity, the genetically engineered recombinant *E. coli* comprising deletion of each of a native xylGFH, rbsACB, and alsBAC operon.

* * * * *